(12) United States Patent
Yamada et al.

(10) Patent No.: US 6,312,759 B1
(45) Date of Patent: Nov. 6, 2001

(54) FLUORINATED HYDROCARBONS, DETERGENTS, DETERGING METHOD, POLYMER-CONTAINING FLUIDS, AND METHOD OF FORMING POLYMER FILMS

(75) Inventors: Toshirou Yamada, Kanagawa; Kuniaki Goto, Tokyo; Tatsuya Sugimoto, Kanagawa, all of (JP)

(73) Assignee: Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 09/423,899

(22) PCT Filed: May 15, 1998

(86) PCT No.: PCT/JP98/02158

§ 371 Date: Apr. 13, 2000

§ 102(e) Date: Apr. 13, 2000

(87) PCT Pub. No.: WO98/51651

PCT Pub. Date: Feb. 19, 1998

(30) Foreign Application Priority Data

May 20, 1997 (JP) .................................................. 9-145891
May 16, 1997 (JP) .................................................. 9-127591

(51) Int. Cl.[7] ............................................................ B05D 5/12
(52) U.S. Cl. ..................... 427/131; 134/42; 427/127; 427/162; 510/101; 510/102; 510/103
(58) Field of Search .................................. 427/127, 131, 427/162; 510/101–103; 134/42

(56) References Cited

FOREIGN PATENT DOCUMENTS

| | | |
|---|---|---|
| 1046095-A | 10/1966 | (GB) . |
| 5-302098 | 11/1993 | (JP) . |
| 5-508418-A | 11/1993 | (JP) . |

(List continued on next page.)

OTHER PUBLICATIONS

Heterocyclic Polyfluoro–compounds. Part XIV. Catalytic Hydrogenqtion of Perflouro–(3–6, dihydro–2–methyl–2H–1, 20oxazine) and of Perfluorocyclopentene, (Banks, R. E. et al.), J. Chem. Soc. ©, 1968, No. 5, pp. 548–550 (No month avail).
Fouorocyclohexanes, Part VIII. Lithium Aluminum Hydride Reduction of Decafluorocyclohanee. (Evans, D. E. M.) J. Chem. Soc., Oct. 1963, pp. 4828–4834.
Abstract of JP 5302098, Nov. 16, 1993.
Bispen, T.A. et al., "Preparation and properties of some polyfluorinated pentanes", Zh. Prikl. Khim. (1995) vol. 68, No. 5, p. 793–796 (No month avail.).
Motnyak, L.A. et al., "Reaction of hydroxy–and carbonyl compounds with sulfur tetrafluoride", Zh. Org. Khim (1983) vol. 19, No. 4, p. 720–726 (No month avail.).
Burmakov, A.I. et al., "Reaction of aliphatic α–hydroxycarboXylic acids with sulfur tetrafluoride", Zh. Org. Khim. (1980) vol. 16, No. 7, p. 1401–1408 (No month avail.).

*Primary Examiner*—Bernard Pianalto
(74) *Attorney, Agent, or Firm*—Wenderoth, Lind & Ponack, L.L.P.

(57) ABSTRACT

Providing a fluorinated hydrocarbon with excellent cleaning action, incombustibility and high stability in alkali or water and heat; and a polymer-containing solution prepared by dissolving or dispersing a polymer with film-forming potency, preferably a fluoropolymer, in a solvent containing trihydrofluorocarbon. More specifically, a fluorinated hydrocarbon containing trihydrofluorocarbon with 4 to 6 carbon atoms at 95% or more, as represented by the following formula, is provided, together with a polymer-containing solution containing the same:

$$Rf_1 - R_1 - Rf_2 \qquad (I)$$

wherein $R_1$ represents a carbon chain of CHF and $CH_2$, bound to each other; $Rf_1$ and $Rf_2$ independently represent a perfluoroalkyl group; and $Rf_1$ and $Rf_2$ may be bound to each other, to form a ring.

48 Claims, 1 Drawing Sheet

FOREIGN PATENT DOCUMENTS

| | | |
|---|---|---|
| 10-71372 | 3/1998 | (JP) . |
| 10-71373 | 3/1998 | (JP) . |
| 92/06941 | 4/1992 | (WO) . |
| 93/16023 | 8/1993 | (WO) . |
| WO-9519947-A1 | 7/1995 | (WO) . |
| 97/05211 | 2/1997 | (WO) . |
| 97/45521 | 12/1997 | (WO) . |
| 97/45522 | 12/1997 | (WO) . |

FLUORINATED HYDROCARBONS, DETERGENTS, DETERGING METHOD, POLYMER-CONTAINING FLUIDS, AND METHOD OF FORMING POLYMER FILMS

This application is a 371 application of PCT/JP98/02158 filed May 15, 1998.

TECHNICAL FIELD

The invention of the present application relates to a fluorinated hydrocarbon, and a cleaning agent and a cleaning method. Additionally, the invention of the application relates to a polymer-containing solution comprising a homogeneously dissolved or dispersed polymer, and a method for forming a polymer film on solid surface by using such solution. More specifically, the invention of the application relates to a fluorinated hydrocarbon comprising trihydrofluorocarbon, a solvent composition useful for cleaning, water draining and drying articles and for dissolving and dispersing a polymer with lubricating properties and the like, and a cleaning agent containing the same as the effective ingredient, a cleaning method for efficiently cleaning off stains from articles such as metal materials, plastic materials, glass materials and ceramic materials, and a polymer-containing solution comprising a homogeneously dissolved or dispersed polymer imparting lubricating properties and the like to solid surface, and a method for forming a polymer film on solid surface by using such solution.

BACKGROUND OF THE INVENTION

As industrial cleaning methods of various materials, conventionally, use has been made in a wide variety of fields of solvent compositions containing CFC113 and 1,1,1,-trichloroethane with excellent incombustibility, low toxicity and good stability as the principal components. However, it has been remarked that various types of CFC, 1,1,1,-trichloroethane, and carbon tetrachloride and the like damage the ozone layer, leading to the absolute worldwide banning of the production of CFC113, 1,1,1-trichloroethane and the like since the end of 1995 and to the use thereof under regulation, from the standpoint of the protection of the ozone layer.

As alternatives of these CFC113 and the like, hydrochlorofluorocarbons such as HCFC225 and HCFC141b have been proposed and used practically. But a time limit is imposed to the use thereof because these have also damaging potencies of the ozone layer although the potencies are extremely low. Furthermore, conventional chlorine containing solvents including for example methylene chloride, trichloroethylene, and perchloroethylene are so problematic in terms of safety profile (oncogenesis and intoxication) that these have been also under various regulations or have been under way of regulatory controls.

Still furthermore, various compounds have been proposed, which can retain the advantages of these fluorine containing solvents, such as incombustibility and stability, but never contain chlorine atom as the essential factor for the ozone layer depletion. The compounds include for example those principally comprising perfluorocarbons such as perfluoro-n-heptane (WO 92-03205, etc.), those principally comprising acyclic hydrofluorocarbons (WO 95-06693, JP-W-6-501949) and those principally comprising specific cyclic hydrofluorocarbons (WO 95-05448).

For the purpose of endowing solid surface with lubricating properties, non-coherent properties, water-repelling properties, conventionally, a method has been used for forming a polymer film with lubricating properties, non-coherent properties, and water-repelling properties on solid surface by using a solution dissolving or dispersing a polymer therein.

As electronic devices, machines and appliances and parts have been down-sized and highly sophisticated, these are required to have high lubricating properties at the sliding parts and surfaces thereof. Lubricating properties and non-coherent properties at high precision, high durability and high reliability have been demanded specifically for sliding between hard disk, mini-disc, magnetic tapes such as digital audio tape or video tape, other magnetic record media or optical disks and record/read-out heads. For sliding between hard disk and record/read-out head, for example, a protective layer of carbon and the like is formed on a magnetic layer; and then, a polymer film comprising a lubricating fluoro polymer is additionally formed thereon. Because the sliding parts of machines and appliances such as cameras, video cameras, office machines, medical apparatuses, vacuum machines such as vacuum pumps, electronic parts, precision automobile parts, small motor, ultrasonic motor and micro-machine should be endowed with lubricating properties with high durability, high reliability and low staining properties, due to the demands for high performance and down-sizing thereof, polymer films comprising lubricating fluorine-series polymers are likely to be formed on the sliding parts of these machines and appliances. So as to securely impart discharge stability and orientation to polar liquids, polymer films comprising water-repellent fluorinated polymers are formed on the nozzle surface on the nozzle opening of inkjet recording head.

Conventionally, various propositions have been made regarding the method for forming polymer films on such solid surfaces. For example, a method comprises dissolving a polymer with a small surface tension, such as fluoro polymer with lubricating properties or water repellency, in an appropriate volatile solvent, coating the resulting solution on various materials or parts, and thereafter vaporizing the solvent to form a polymer film.

A solution prepared by dissolving a fluoro polymer in a fluorinated solvent has been known. CFC 113 (JP-A-5-342570) and perfluoro-n-heptane (JP-A-4-211959) are reported as such fluorinated solvents. However, the production and marketing of conventional CFC 113 is prohibited under the regulation against ozone layer layer-depletion substances, while perfluorocarbons such as perfluoro-n-heptane are disadvantageous because of the poor solubility so that a uniform fluorinated polymer film cannot be recovered.

JP-A-3-158884 describes a process of coating a dispersion prepared by dispersing polyvinylidene fluoride, a phenolic resin or tospearl in particles in a liquid medium selected from isopropyl alcohol, ethyl alcohol, CFC 113 and water on the contact part between the image carrier in an imaging apparatus and a member material in contact to the image carrier, and subsequently drying the dispersion. It is described that according to the process, the friction between the image carrier and a cleaning blade in contact to the carrier can be reduced, leading to the resolution of problems including blade peel off or non-uniformly charged state of the surface of the image carrier.

JP-A-3-197952 describes a process of spraying a dispersion of particles such as fluorine resin particles or silicone resin particles in an organic solvent on the surface of an electrophotographic photosensitive material and then drying the dispersion. The organic solvent including CFCs is exemplified. It is described that according to the process, the friction between the photosensitive material and the cleaning blade for removing residual toner is reduced, whereby the problem of blade peel off can be overcome.

Because these polymers with lubricating properties are not homogeneously dispersed or dissolved in the polymer-containing solutions, polymer films prepared by coating the polymer-containing solutions on solid surface and removing the liquid medium are not uniform on the solid surface. Hence, the effect of the polymer films to reduce friction on the solid surface cannot be exerted sufficiently.

As has been described above in detail, the perfluorocarbons and hydrofluorocarbons are preferable in terms of no concern of the ozone layer depletion, and good cleaning performance with great finish, when used as they are or in combination with organic solvents. Nevertheless, they individually have problems to be overcome. For example, perfluorocarbons have high global warming potentials, leading to the possible occurrence of new problems from the standpoint of the protection of global environment. Additionally, cyclic or acyclic hydrofluorocarbons of various structures have been proposed, but they are problematic, structurally. For example, hydrofluorocarbons of a structure with a $—CF_2CHFCHFCF_2—$ bond are disadvantageous in terms of poor stability in the presence of basic compounds or water.

It is the object of the first aspect of the invention of the application to provide a fluorinated hydrocarbon with excellent cleaning performance, great incombustibility and high stability in the presence of water, which can overcome the drawbacks of such conventionally known hydrofluorocarbons and can be produced readily, a method for producing the same and a solvent composition thereof, and a cleaning agent and a cleaning method, using the same.

It is the object of the second aspect of the invention of the application, to provide a polymer-containing solution and the like capable of forming a uniform polymer film on solid surface by sufficiently enhancing the homogenous dissolution of a polymer in the polymer-containing solution, and a process of forming a polymer film using the same, because a polymer-containing solution capable of forming a uniform polymer film on solid surface has been desired although conventional techniques for forming polymer film as described above can exert only a limited effect on the improvement of solid surface.

DISCLOSURE OF THE INVENTION

So as to overcome the problems, in accordance with the invention of the application, it is provided a fluorinated hydrocarbon containing cyclic trihydrofluorocarbon with 5 carbon atoms and a purity of 95% by weight or more, as represented by the following formula(I):

$$Rf_1—R_1—Rf_2 \qquad (I)$$

wherein $R_1$ represents a carbon chain of CHF and $CH_2$, bound to each other; $Rf_1$ and $Rf_2$ are bound to each other to form a ring of a perfluoroalkylene chain.

In accordance with the invention of the application, a method for producing the fluorinated hydrocarbon, comprising subjecting dihydrofluorocarbon represented by the following formula II to an alkali treatment and hydrogenating the resulting product is provided:

$$Rf_1—CHF—CHF—Rf_2 \qquad (II)$$

wherein $Rf_1$ and $Rf_2$ independently represent a perfluoroalkyl group and $Rf_1$ and $Rf_2$ may be bound to each other, to form a ring. Additionally, the invention of the application provides a cleaning agent containing the fluorinated hydrocarbon or a solvent composition thereof as the effective ingredient, a method for cleaning articles, comprising a step of removing staining substances deposited on articles by putting the articles in contact to an organic solvent comprising at least one selected from hydrocarbons, alcohols, esters, chlorinated hydrocarbons, fluorinated hydrocarbons, ethers, ketones, and volatile organic silicones, and a step of rinse cleaning the articles, comprising putting the organic solvent deposited on the articles after the removal of the staining substances in contact to the cleaning agent, thereby rinse cleaning the articles, or comprising a step of vapor cleaning the articles in the vapor of the cleaning agent.

Additionally, the invention of the application provides a polymer-containing solution prepared by dissolving or dispersing a polymer with film-forming potency in an organic solvent containing the fluorinated hydrocarbon or a solvent composition thereof. Furthermore, the invention of the application provides a method for forming a polymer film on solid surface, comprising coating the polymer-containing solution on the solid surface and removing the liquid medium.

BRIEF DESCRIPTION OF THE DRAWINGS

The FIGURE is a composition figure depicting one example of the apparatus for rinsing and cleaning in accordance with the application, wherein the symbols represent those described below:

1. cleaning vessel 1
2. cleaning vessel 2
3. rinse cleaning vessel
4. separator
5. vapor cleaning vessel
6. cleaning agent layer
7. trihydrocarbon layer
8. vapor zone
9. heating apparatus
10. ultrasonic oscillation apparatus
11. circulation pump
12. circulation pump
13. cooling coil
14. rinse solution transfer pump
15. destillation column

BEST MODE FOR CARRYING OUT THE INVENTION

Figure 1:
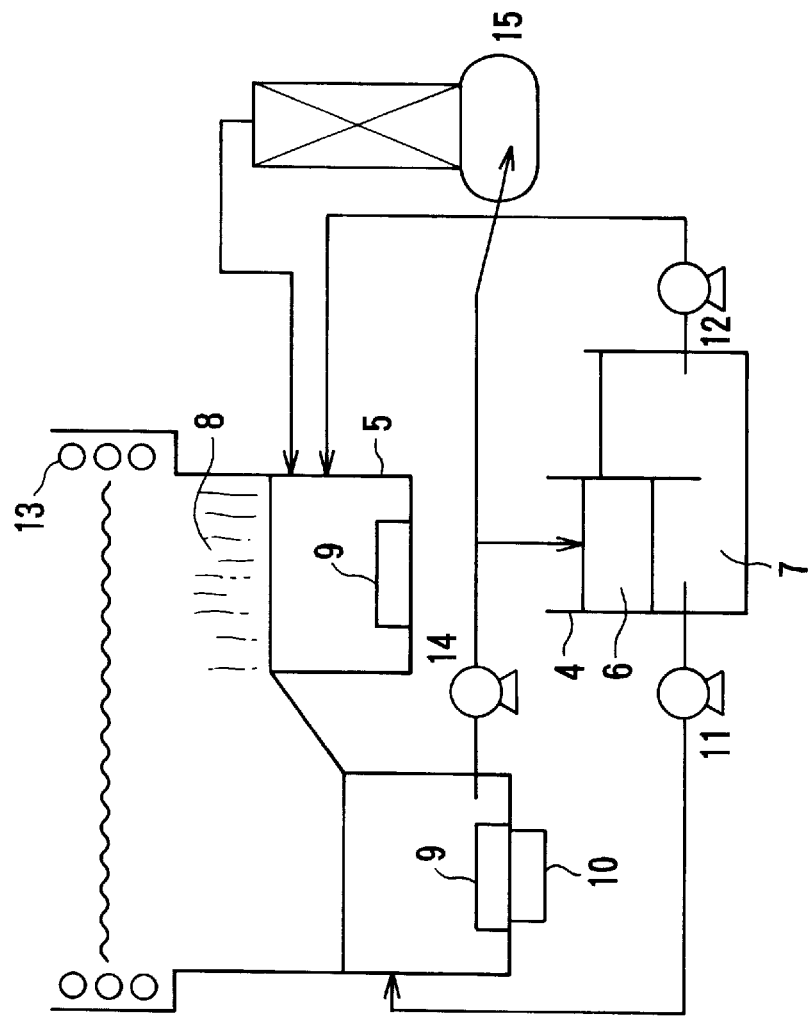
Figure 1:
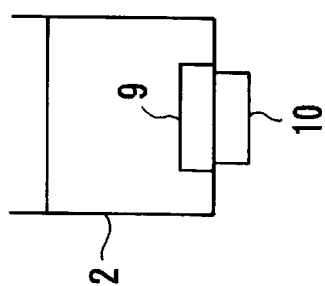
Figure 1:
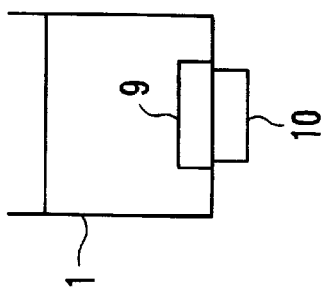

As described above, the fluorinated hydrocarbon of the invention characteristically comprises a cyclic trihydrofluorocarbon with 5 carbon atoms and a purity of 95% by weight or more, wherein 3 hydrogen atoms bind onto two adjacent carbon atoms. The inventive fluorinated hydrocarbon comprising such cyclic trihydrofluorocarbon at a high purity of 95% by weight or more has never been known so far or has never been provided in a practical sense, although the flourinated hydrocarbon contains an extremely small amount of other fluorocarbons. This is due to the facts that any specific production method thereof has never been established and that the excellent characteristic properties of the cyclic trihydrofluorocarbon or any applicability thereof to cleaning or lubrication has never been known.

The number of carbon atoms in the trihydrofluorocarbon of this invention represented by the formula I is 5, is preferably at a boiling point of 25° C. or more to 150° C. or less, particularly preferably at a boiling point of 50° C. or more to 100° C. or less. Such fluorinated hydrocarbon is cyclic.

The inventive fluorinated hydrocarbon comprising this cyclic trihydrofluorocarbon at a high purity is inflammable, highly stable in the presence of basic compounds and water and applicable as a cleaning agent of material surface, due to the characteristic properties of cyclic trihydrofluorocarbons and is thus useful as a liquid medium for forming a lubricating polymer film capable of significantly reducing friction on solid surface.

In accordance with the invention, the cyclic trihydrofluorocarbon represented by the formula I is contained at a high content of 95% by weight or more. Possibly, other contaminating fluorocarbons include saturated or unsaturated perfluorocarbons and hydrofluorocarbons being inevitably contained therein at the production process and having the same number of carbon atoms.

As described above, the invention also provides a method of producing a fluorinated hydrocarbon which comprises subjecting dihydrofluorocarbon represented by the formula II to an alkali treatment and subsequently hydrogenating the resulting product. For the alkali treatment of the method, any treatment agent at alkalinity may be used with no specific limitation and includes for example metal hydrogen carbonate salts such as sodium hydrogen carbonate and potassium hydrogen carbonate; metal carbonate salts such as lithium carbonate, sodium carbonate, potassium carbonate, calcium carbonate, magnesium carbonate and barium carbonate; hydroxides such as lithium hydroxide, sodium hydroxide, potassium hydroxide, calcium hydroxide, magnesium hydroxide and barium hydroxide; anion exchange resins; ammonia and amines such as triethylamine and morpholine; and alkali metal compounds such as metal alkoxides and Grignard's reagent. Among them, preference is given to metal hydrogen carbonate salts and metal carbonate salts.

As to the amount of an alkali to be used, the alkali is used at an equivalent amount or more to one mole of the dihydrofluorocarbon. Any reaction temperature is satisfactory, with no specific limitation, but generally, the reaction temperature is about 0 to 100° C., preferably about 10 to 80° C. For the alkali treatment, furthermore, a reaction additive may satisfactorily be added. The additive is preferably an phase transfer catalyst. Any phase transfer catalyst is satisfactory, with no specific limitation, as long as the catalyst is generally used for synthetic reaction; the phase transfer catalyst includes for example quaternary salts such as quaternary ammonium halides and quaternary phosphonium halides; polyethers such as crown ethers and polyoxyalkylene glycols; and aminoalcohols. Quaternary salts are particularly preferable.

The quaternary salts comprise a cation (positive ion) prepared by binding four substituents containing carbon atom to a hetero atom such as nitrogen atom and phosphorus atom, and a pair anion (negative ion).

These phase transfer catalysts may be used singly or in combination with two or more thereof.

The alkali treatment in accordance with the invention may be carried out in two layers of water and the dihydrofluorocarbon, satisfactorily, but a part or the entirety thereof may be substituted with a polar solvent. The polar solvent includes for example alcohols such as methanol, ethanol and isopropanol; glycols such as ethylene glycol; glycol ethers such as ethylene glycol monomethyl ether; sulfoxides such as dimethyl sulfoxide; sulfolanes; amides such as dimethylformamide, dimethylacetamide and N-methylpyrrolidone; and ureas such as dimethylimidazolidinone.

Furthermore, the subsequent hydrogenation is preferably carried out by using for example noble metal catalysts and the like at atmospheric pressure to a pressure of about 10 kgf/cm$^2$ and a reaction temperature of ambient temperature to about 350° C., with no specific limitation alike. Still further, liquid phase reaction or gas phase reaction may be selected appropriately for the reaction.

As the noble metal catalysts, generally, use is made of a noble metal immobilized on a carrier. The noble metal herein referred to includes palladium, rhodium, ruthenium, rhenium or platinum, and is preferably palladium, rhodium or ruthenium. These raw metals may be used singly or in the form of an alloy in combination with two or more thereof, namely so-called bimetal catalyst. The type, shape and size of the carrier are not specifically limited, but preferably, the carrier is active charcoal, alumina or titanium, in powder or in a molded article in sphere or pellet.

The amount of the noble metal immobilized on the carrier is generally 0.5 to 20% by weight, but preferably, it is recommended that the amount thereof is 1 to 20% by weight, provided that the carrier is powdery or that the amount is 1 to 10% by weight, provided that the carrier is a molded article. More preferably, a powdery catalyst at an immobilization amount of 1 to 10% by weight is recommended, whereby a fluorinated hydrocarbon at a cyclic trihydrofluorocarbon content of 95% by weight can be produced.

The raw material dihydrofluorocarbon represented by the formula II can readily be prepared by hydrogenation and the like of the corresponding perfluoroolefin (cycloolefin).

The inventive fluorinated hydrocarbon substantially comprising cyclic trihydrofluorocarbon or containing the same as the principal component is obtained as one kind of product of the production method as described above, but may compose a solvent composition substantially containing cyclic trihydrofluorocarbon alone but inevitably containing negligible byproducts or impurities inevitably produced at the production process or preparation process of the composition or containing the cyclic trihydrofluorocarbon as the principal component.

The composition of the fluorinated hydrocarbon comprising cyclic trihydrofluorocarbon or containing the same as the principal component with a solvent is useful as a cleaning agent or for preparing polymer-containing solutions and the like. For these applications, the composition effectively contains at least one organic solvent at a boiling point of 25° C. or more to 250° C. or less. Such organic solvent is added at any amount, with no specific limitation, but generally, the amount is at 50% by weight or less, preferably 2 to 30% by weight and more preferably 3 to 20% by weight to the total weight. When the trihydrofluorocarbon or the fluorinated hydrocarbon containing the same as the principal component and such organic solvent together are allowed to form an azeotropic composition, these are used at amounts for preparing an azeotropic composition.

Along with hydrocarbons, alcohols, esters, halogenated hydrocarbons, ethers and ketones, the inventive fluorinated hydrocarbon comprising cyclic trihydrofluorocarbon or containing the same as the principal component forms an azeotropic composition.

When the inventive cyclic trihydrofluorocarbon is 1,1,2, 2,3,3,4-heptafluorocyclopentane, for example, an azeotropic composition is formed together with hydrocarbons such as n-octane, 2,2,4-trimethylpentane, and n-heptane; alcohols such as methanol, ethanol, isopropanol, 1-butanol and 2-butanol; chlorinated hydrocarbons such as trichloroethylene and tetrachloroethylene; and other fluorinated hydrocarbons such as ethyl perfluorobutyl ether and perfluorooctane.

More specifically, the azeotropic temperature of the azeotropic composition of 1,1,2,2,3,3,4-heptafluorocyclopentane and n-octane is 79° C., wherein the composition ratio of n-octane is 7.8% by weight. The azeotropic temperature of the azeotropic composition of 1,1,2,2,3,3,4-heptafluorocyclopentane and 2,2,4-trimethylpentane is 75° C., wherein the composition ratio of 2,2,4-trimethylpentane is 21.2% by weight. The azeotropic temperature of the azeotropic composition of 1,1,2,2,3,3,4-heptafluorocyclopentane and n-heptane is 73° C., wherein the composition ratio of n-heptane is 12.8% by weight. The azeotropic temperature of the azeotropic composition of 1,1,2,2,3,3,4-heptafluorocyclopentane and methanol is 60° C., wherein the composition ratio of methanol is 23.1% by weight. The azeotropic temperature of the azeotropic composition of 1,1,2,2,3,3,4-heptafluorocyclopentane and ethanol is 69° C., wherein the composition ratio of ethanol is 18.4% by weight. The azeotropic temperature of the azeotropic composition of 1,1,2,2,3,3,4-heptafluorocyclopentane and isopropanol is 73° C., wherein the composition ratio of isopropanol is 19.6% by weight. The azeotropic temperature of the azeotropic composition of 1,1,2,2,3,3,4-heptafluorocyclopentane and 1-butanol is 80° C., wherein the composition ratio of 1-butanol is 2.3% by weight. The azeotropic temperature of the azeotropic composition of 1,1,2,2,3,3,4-heptafluorocyclopentane and 2-butanol is 79° C., wherein the composition ratio of 2-butanol is 8.4% by weight. The azeotropic temperature of the azeotropic composition of 1,1,2,2,3,3,4-heptafluorocyclopentane and trichloroethylene is 73° C., wherein the composition ratio of trichloroethylene is 21.3% by weight. The azeotropic temperature of the azeotropic composition of 1,1,2,2,3,3,4-heptafluorocyclopentane and tetrachloroethylene is 79° C., wherein the composition ratio of tetrachloroethylene is 7.3% by weight. The azeotropic temperature of the azeotropic composition of 1,1,2,2,3,3,4-heptafluorocyclopentane and trans-1,2-dichloroethylene is 46° C., wherein the composition ratio of trans-1,2,-dichloroethylene is 84% by weight. The azeotropic temperature of the azeotropic composition of 1,1,2,2,3,3,4-heptafluorocyclopentane and ethyl perfluorobutyl ether is 74° C., wherein the composition ratio of ethyl perfluorobutyl ether is 75.3% by weight. The azeotropic temperature of the azeotropic composition of 1,1,2,2,3,3,4-heptafluorocyclopentane and perfluorooctane is 78° C., wherein the composition ratio of perfluorooctane is 34.2% by weight.

For the application to a cleaning agent in another aspect of the invention, the fluorinated hydrocarbon comprising cyclic trihydrofluorocarbon or containing the same as the principal component can be used in a composition with hydrocarbons, alcohols, esters, chlorinated hydrocarbons, brominated hydrocarbons, other fluorinated hydrocarbons, ethers, and ketones. Preferably, the fluorinated hydrocarbon comprising cyclic trihydrofluorocarbon or containing the same as the principal component can be used in an azeotropic composition with hydrocarbons, alcohols, esters, chlorinated hydrocarbons, other fluorinated hydrocarbons, ethers, and ketones. More preferably, the fluorinated hydrocarbon comprising cyclic trihydrofluorocarbon or containing the same as the principal component can be used in a azeotropic composition with alcohols or hydrocarbons or chlorinated hydrocarbons or other fluorinated hydrocarbons. Most preferably, 1,1,2,2,3,3,4-heptafluorocyclopentane can be used in an azeotropic composition with 1-butanol, 2-butanol, n-octane, 2,2,4-trimethylpentane, n-heptane, trichloroethylene, tetrachloroethylene, ethyl perfluorobutyl ether, and perfluorooctane.

The inventive fluorinated hydrocarbon or cyclic trihydrofluorocarbon and a solvent composition comprising the same are most characteristically applied as a cleaning agent or a polymer-containing solution; for example, the cleaning agent characteristically contains the inventive fluorinated hydrocarbon or cyclic trihydrofluorocarbon as the effective ingredient.

Any type of organic solvents may be used for preparing solvent compositions, with no specific limitation, and includes at least one organic solvent selected from for example hydrocarbons, alcohols, esters, chlorinated hydrocarbons, other fluorinated hydrocarbons, ethers, ketones, and volatile organic silicones.

With no specific limitation, the hydrocarbons include for example aliphatic hydrocarbons such as n-pentane, n-hexane, n-heptane, isohexane, isoheptane, n-octane, isooctane, n-decane, isodecane, n-undecane, n-dodecane, and n-tridecane; alicyclic hydrocarbons such as cyclopentane, methylcyclopentane, cyclohexane, and methylcyclohexane; and aromatic hydrocarbons such as benzene, toluene and xylene.

With no specific limitation, the alcohols include for example methanol, ethanol, isopropanol, n-propanol, n-butanol, s-butanol, t-butanol, n-pentanol, isopentanol, n-hexanol, isohexanol, 2-ethylhexanol and n-octanol. Among them, preference is given to alcohols with 5 or less carbon atoms; and furthermore, alcohols with 1 to 4 carbon atoms are specifically preferable.

With no specific limitation, the esters include for example methyl acetate, ethyl acetate, propyl acetate, isopropyl acetate, butyl acetate, isobutyl acetate, pentyl acetate, methylpropionic acid, ethylpropionic acid, propylpropionic acid, isopropylpropionic acid, methylbutylic acid, ethylbutylic acid, isopropylbutylic acid, methylvaleric acid and ethylvaleric acid. Among them, preference is given to esters with 3 to 10 carbon atoms, particularly esters with 3 to 6 carbon atoms.

With no specific limitation, the chlorinated hydrocarbons include for example methylene chloride, dichloroethane, dichloroethylene, trichloroethylene and perchloroethylene.

With no specific limitation, other fluorinated hydrocarbons may principally be composed of carbon, hydrogen and fluorine and may satisfactorily contain oxygen atom or unsaturated bonds. Among them, fluorinated hydrocarbons at a boiling point of 25° C. or more are preferable and include for example pentafluoropropane, hexafluorobutane, decafluoropentane, hexafluorocyclopentane, octafluorocyclopentane, perfluoropropyl methyl ether, perfluorobutyl methyl ether, perfluorobutyl ethyl ether, hexafluorocyclopentene, heptafluorocyclopentene and octafluorocyclopentene. Furthermore, preference is given to hexafluorocyclopentane, octafluorocyclopentane and hexafluorocyclopentene, because of the cyclic structures and the appropriate boiling points.

With no specific limitation, the ketones include for example acetone, 2-butanone, 2-pentanone, 3-pentanone, 2-hexanone, 3-methyl-2-butanone, cyclopentanone, cyclohexanone, 2-methylcyclopentanone and 2-methylcyclohexanone.

The volatile organic silicones include hexamethyldisiloxane, ocatamethyltrisiloxane, decamethyltetrasiloxane, hexamethylcyclotrisiloxane, octamethylcyclotetrasiloxane, and decamethylcyclopentasiloxane.

Still furthermore, conventionally known various additives can be added to the inventive cleaning agent. The additives include for example stabilizers and surfactants. With no specific limitation, the stabilizers specifically include aliphatic nitro compounds such as nitromethane and nitroethane; acetylene alcohols such as 3-methyl-1-butyn-3-ol, and 3-methyl-1-pentyn-3-ol; epoxides such as glycidol, methyl glycidyl ether and acrylglycidyl ether; ethers such as dimethoxymethane and 1,4-dioxane; unsaturated hydrocarbons such as hexene, heptene, cyclopentene and cyclohexene; unsaturated alcohols such as allyl alcohol and 1-buten-3-ol; and acrylate esters such as methyl acrylate and ethyl acrylate.

As the surfactants, then, use can be made of known anion activators, cation activators, nonion activators and amphoteric activators. The anion activators include for example carboxylate salts, sulfonate salts, sulfate ester salts, and phosphate ester salts. The cation activators include for example amine salts of various acids and quaternary ammonium salts. The nonionic activators include for example polyoxyethylene ether, polyoxyethylene-polyoxypropylene glycol, polyoxyethylene-polyoxypropylene alkyl ether, and esters of fatty acid moieties of polyhydric alcohols. The amphoteric activators include for example betaines, amino organic acids and amine salts of fatty acids.

Additionally, activators comprising these compounds containing fluorine atom in the molecules are preferable. When these surfactants are added, deposited water on processed parts comprising metals, ceramics, glass, and plastic elastomers can effectively be removed after water cleaning, so these parts can be dried.

With no specific limitation, the amount of these surfactants to be added is generally at 30% by weight or less, preferably 20% by weight or less and more preferably 0.005 to 10% by weight to the total weight.

With no specific limitation, the cleaning subject materials in accordance with the invention include for example processed parts comprising metal, ceramics, glass, plastic and elastomers in precision machine industries, metal processing industries, optical device industries, electronics, and plastic industries. More specifically, a wide variety of examples are illustrated, including automobile parts such as bumper, gear, mission parts and radiator parts; electronic and electric devices such as printed circuit boards, IC parts, lead frames, motor parts and condensers; precision machine parts such as bearings, gears, empra gears, clock parts, camera parts and optical lens; printers, printer blades, print rolls, press products, building machines, glass substrates, parts of large machines such as large heavy-duty machines, daily products such as dishes, and fiber products.

The staining substances include various types, for example oils such as cutting oil, hardening oil, press oil, lubrication oil, machine oil, press processing oil, punching oil, drawing oil, fabrication oil and lining oil; greases, waxes, adhesives, fatly acid esters, release agents for molding, finger mark; and fluxes, resists, and solder pastes after soldering.

The cleaning method satisfactorily comprises putting a cleaning subject material in contact to the cleaning solvent composition. General cleaning methods are applicable. More specifically, for example, methods by hand wiping, immersion, spraying and shower are applicable. For these treatments, if necessary, physical means such as ultrasonic vibration, shaking, agitation and brushing may be used in combination.

For cleaning, an organic solvent comprising at least one selected from aliphatic hydrocarbons, alicyclic hydrocarbons, aromatic hydrocarbons, alcohols, esters, chlorinated hydrocarbon, ethers, ketones and volatile organic silicones can be used satisfactorily as another solvent different from the cleaning agent in accordance with the invention.

In this case, a method comprising two steps, namely a step of removing staining substances from a cleaning subject material and a step of cleaning and rinsing off the organic solvents deposited on the material after removal of the staining substances by putting the material in contact to the inventive solvent or by vapor cleaning the material in the vapor of the cleaning agent, is selectively used and includes for example the following cleaning method (so-called co-solvent system).

Co-solvent system (1) Cleaning step

At the first step, a cleaning subject material is cleaned in a cleaning agent comprising as the principal component at least one organic solvent selected from hydrocarbons, alcohols, ethers, ketones and volatile organic silicones.

The hydrocarbons include for example aliphatic hydrocarbons and aromatic hydrocarbons, which are saturated acyclic, unsaturated acyclic, saturated cyclic or unsaturated cyclic; among them, aliphatic hydrocarbons are preferable; and particularly preferable are aliphatic hydrocarbons, saturated acyclic and unsaturated cyclic. The number of carbon atoms in these hydrocarbons may appropriately be selected, depending on the cleaning use (purpose). Generally, the number is 5 to 30, preferably 8 to 20 and more preferably 10 to 15.

These hydrocarbons include for example saturated acyclic aliphatic hydrocarbons, such as pentane, hexane, heptane, octane, isooctane, nonane, decane, isodecane, undecane, dodecane, isododecane, tridecane, tetradecane, pentadecane, hexadecane, heptadecane, octadecane and isooctadecane; saturated cyclic hydrocarbons such as cyclopentane, methylcyclopentane, cyclohexane, methylcyclohexane, cyclodecane, methylcyclodecane, cyclododecane, decalin, and norbornane; unsaturated hydrocarbons in chain, such as heptene, heptadiene, octene, octadiene, nonene, nonadiene, decene, decadiene, undecene, dodecane, dodecadiene, tridecene, tridecadiene, tetradecene, tetradecadiene, octadecene, octadecadiene, and isoprene dimer; cyclic unsaturated hydrocarbons including terpenes, such as α-pinene, β-pinene, γ-terpinene, δ-3-carene, limonene, and dipentene; and aromatic hydrocarbons such as toluene. Among them, preference is given to decane, undecane, dodecane, tridecane, tetradecane, pentadecane, limonene, and dipentene. These hydrocarbons can be used singly or in combination with two or more thereof. As commercially available hydrocarbon cleaning solvents, use can be made of Normal Paraffin series, Isozol series, and Isolan series (manufactured by Nippon Petroleum Co., Ltd.), Solbents Nos. 0 to 5 and Teclean Series (Nippon Petroleum Co., Ltd.), NS Clean Series (manufactured by Nikko Petroleum Chemical Industries, Co. Ltd.) and the like.

Cleaning solvents containing these hydrocarbons as the principal ingredients can be used. The solvents contain only hydrocarbons or contain various additives in addition to the base hydrocarbons, like cutting oil, lubrication oil, machine oil and press processing oil.

The alcohols include for example alcohols where at least one hydroxyl group is bound to a hydrocarbon residue, saturated acyclic, unsaturated acyclic, saturated cyclic or unsaturated cyclic. These hydrocarbon residues may contain a functional group such as alkoxyl group. The number of carbon atoms in the hydrocarbon residue is appropriately selected, depending on the purpose of cleaning, and generally, the number is 1 to 15, preferably 4 to 10. Such alcohols include methanol, ethanol, propanol, isopropanol, isopropanol, butanol, hexanol, 1-hexenol, 2-ethylhexanol, cyclopentanol, cyclohexanol, decyl alcohol, ethylene glycol, 1,2-propane diol, 1,2-cyclopentane diol, ethylene glycol monomethyl ether, and ethylene glycol monobutyl ether.

The ethers include for example ethers where at least one alkoxyl group is bound to a hydrocarbon residue, saturated acyclic, unsaturated acyclic, saturated cyclic and unsaturated cyclic; additionally, the ethers include ethers where oxygen and a carbon chain together may satisfactorily form a cyclic structure. The number of carbon atoms is appropriately selected, depending on the purpose of cleaning; and the number is generally 4 to 15, preferably 4 to 10. Such ethers include diethyl ether, diisopropyl ether, dibutyl ether, tetrahydrofuran, 1,3-dioxane, trioxane, cyclopentyl methyl ether, cyclohexyl ethyl ether, ethylene glycol dimethyl ether, ethylene glycol diethyl ether, and diethylene glycol dimethyl ether.

As the volatile organic silicon, additionally, use is made of a volatile organic silicone substantially comprising at least one low molecular polyorganosiloxane selected from linear or cyclic polydiorganosiloxane represented by the following formulas 1 and 2:

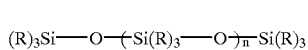
(1)

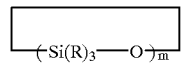
(2)

wherein R may be the same or different and represent a monovalent organic group, substituted or unsubstituted; n represents an integer of 0 to 3; and m represents an integer of 3 to 5.

The R in the formulas includes for example alkyl groups such as methyl group, ethyl group, propyl group and butyl group; aryl groups such as phenyl group; substituted alkyl groups such as trifluoromethyl group and pentafluoroethyl group; lower alkoxyl groups such as methoxy group and ethoxy group; carbonyl-containing groups such as methyoxycarbonyl group, ethoxycarbonyl group and acetyl group; and amide group. From the respect of compound stability, preference is given to methyl group, ethyl group, methoxy group and ethoxy group. Methyl group is the most preferable.

As to n and m in number in the formulas, preferably, n is 0 or more and m is 3 or more, from the respects of formation of silicone structure and of cyclic stability for cyclic polydiorganosiloxane. Preferably, n is 3 or less and m is 5 or less, whereby the resulting cleaning agent can be subjected to distillation in a practical sense for recycling.

Such silicon containing cleaning agent includes for example, hexamethyldisiloxane, octamethyltrisiloxane, decamethyltetrasiloxane, hexamethylcyclotrisiloxane, octamethylcyclotetrasiloxane, and decamethylcyclopentasiloxane. Among them, preference is given to octamethylcyclotetrasiloxane, in particular, from the respect of physico-chemical properties such as boiling point and surface tension. If necessary, surfactants and water can be added to these cleaning agents.

Furthermore, the cleaning agent can be used in repetition, after distillation and recovery. In this case, cleaning solutions described below may partially be contained in the resulting recovered product, with no problem.

The cleaning method satisfactorily comprises putting a cleaning subject material in contact to the cleaning solvent, according to general cleaning processes. Specifically, the cleaning processes include hand wiping, immersion, spraying, and shower; immersion process is particularly preferably used. For immersion treatment, physical means such as ultrasonic vibration, shaking, agitation, and brushing can be used in combination. The temperature of the cleaning solvent may appropriately be selected, depending on the properties of the cleaning subject material. Generally, the temperature is within a range of ambient temperature to the boiling point thereof, preferably 40° C. or more to the boiling point, and more preferably 50° C. or more to the boiling point.

(2) Rinse cleaning process

After the above cleaning process, the cleaning subject material, on which the cleaning solvent is deposited, is then rinse cleaned by using a cleaning agent containing the inventive fluorinated hydrocarbon comprising cyclic trihydrofluorocarbon at a high purity of containing cyclic trihydrofluorocarbon per se, as the principal ingredient.

By using the inventive high-purity cyclic trihydrofluorocarbon as the rinse cleaning solvent, the rinse cleaning power of hydrocarbon can be prominently improved, compared with acyclic hydrofluorocarbon or perfluorocarbon. The difference in the effect can be distinctively exerted when cleaning subject materials are continuously cleaned.

The inventive cyclic trihydrofluorocarbon can be used singly or in combination with two or more types thereof.

The rinse cleaning agent containing the fluorinated hydrocarbon or cyclic trihydrofluorocarbon as the principal ingredient is used in accordance with the invention, as described above, but a single type of cyclic trihydrofluorocarbon (a single type of cyclic trihydrofluorocarbon or a mixture of two or more types of cyclic trihydrofluorocarbon) or a combination of cyclic trihydrofluorocarbon with another organic solvent can be used. Another organic solvent includes those generally used as rinse cleaning solvents, for example linear saturated hydrocarbons such as hexane, octane and isooctane; cyclic saturated hydrocarbons such as cyclopentane and cyclohexane; aromatic hydrocarbons such as toluene and xylene; lower alcohols such as methyl alcohol, ethyl alcohol, propyl alcohol, and isopropyl alcohol; ketones such as acetone and methyl ethyl ketone; ethers such as dimethyl ether and diethyl ether; esters such as vinyl acetate; acyclic hydrofluorocarbons, such as 1,1,1,2,2,3,4,5,5,5-decafluoropentane; and perfluorocarbons such as perfluorohexane and perfluoroheptane. These other organic solvents can be used singly or in combination of two or more thereof; these are used at an amount appropriately selected within a range with no adverse effects on the effect of the invention; generally, the amount is 40% by weight or less, preferably 20% by weight or loss, more preferably 10% by weight or less to the total weight of the rinse cleaning agent.

The rinse cleaning process satisfactorily comprises putting a cleaning subject material in contact to the cleaning solvent, according to general cleaning processes. Specifically, the cleaning processes include hand wiping, immersion, spraying, and showering; immersion process is particularly preferably used. For immersion treatment, physical means such as ultrasonic vibration, shaking, agitation, and brushing can be used in combination. These rinse cleaning processes can be used singly or in combination with two or more thereof. The temperature of the rinse cleaning solvent may appropriately be selected, depending on the properties of the cleaning subject material. Generally, the temperature is within a range of ambient temperature to the boiling point thereof, preferably 40° C. or more to the boiling point, and more preferably 50° C. or more to the boiling point.

(3) Separation process

The rinse cleaning agent for use in rinse cleaning in the process 2 above is concentrated during use in repetition, leading to the decrease of the rinse cleaning power. Thus, the concentrated cleaning agent should necessarily be removed. The method for removing the agent includes two-layer separation method and distillation separation method.

As to the two-layer separation method, due to the difference in specific gravity between the hydrocarbon used in the process 1 and the cyclic trihydrofluorocarbon used in the process 2, the upper hydrocarbon layer is separated from the lower cyclic trihydrofluorocarbon layer. The hydrocarbon can be removed by adding fresh cyclic trihydrofluorocarbon to the same container to overflow and remove the upper hydrocarbon layer. A method is preferably performed, comprising transferring a part of the rinse cleaning solvent in the process 2 to another container, where two layers, namely a hydrocarbon layer and a cyclic trihydrofluorocarbon layer, are separated from each other, and recovering the cyclic trihydrofluorocarbon layer as the lower layer and recycling the layer into the rinse cleaning solvent in the process 2. For two-layer separation, centrifugation process may satisfactorily be used.

The cyclic trihydrofluorocarbon for use in accordance with the invention has such a property that the cyclic trihydrofluorocarbon greatly dissolves hydrocarbon at high temperature but hardly dissolves hydrocarbon at low temperature, like hydrofluorocarbon and perfluorocarbon. Accordingly, the two-layer separation procedure is preferably conducted at a lower temperature; the procedure is generally carried out at a temperature lower by 10° C. or less, preferably 20° C. or less, more preferably 30° C. or less than the temperature of the rinse cleaning solvent. The lower limit temperature for the two-layer separation procedure is preferably above the melting point of the hydrocarbon or cyclic trihydrofluorocarbon. The method for cooling the rinse cleaning solvent is with no specific limitation, and any of the following methods can be used; a method comprising leaving the solvent to stand at ambient temperature, a method comprising cooling the solvent with a cooling medium, and a method comprising partially evaporating cyclic trihydrofluorocarbon and cooling the solvent by means of the evaporation heat. The cooling velocity is with no specific limitation. From the standpoints of efficiency and the prevention of the loss of the cleaning solution, however, active cooling methods such as cooling from outside and evaporation under reduced pressure are recommended.

As a rinse cleaning solvent at the process 2 or as a vapor cleaning solvent at the process 4 described below, the cyclic trihydrofluorocarbon layer recovered through the two-layer separation can be used, as it is or after treatment by distillation, filtration, active charcoal process and drying, if necessary.

Generally, it is very difficult to separate the cleaning agent comprising a substance excluding hydrocarbon into two layers of cyclic trihydrofluorocarbon and a cleaning solvent. Hence, separation by distillation is preferable.

(4) Vapor cleaning process

Vapor cleaning can be carried out in a conventional manner. The vapor cleaning solvent is with no specific limitation. Any vapor cleaning solvent for use in general vapor cleaning can be used with no specific limitation. Because the cyclic trihydrofluorocarbon recovered at the process 3 is highly pure, the cyclic trihydrofluorocarbon can be used as a vapor cleaning solvent, in accordance with the invention; after vapor cleaning, furthermore, the cyclic trihydrofluorocarbon can be circulated as a rinse cleaning solvent at the process 2.

FIG. 1 depicts one example of the cleaning apparatus for the processes described below.

A cleaning subject material with deposited staining substances such as oil, wax and flux, is immersed in a cleaning agent placed in first cleaning vessel 1, where the staining substances deposited on the surface of the cleaning subject material are removed. The cleaning solvent placed in the cleaning vessel 1 can be heated with heating apparatus 9 or cleaned in an ultrasonic manner by means of ultrasonic oscillation apparatus, if necessary, for improving the cleaning power.

When sufficient cleaning effect cannot be yielded in the cleaning vessel 1, the material can be cleaned in cleaning vessel 2. In the cleaning vessel 2 as in the cleaning vessel 1, if necessary, heating and ultrasonic cleaning can be additionally carried out. FIG. 1 depicts two cleaning vessels, but one vessel may be used or two or more vessels may be used in combination, with no specific limitation.

The cleaning subject material, on which the cleaning solvent is deposited after completion of cleaning, is then immersed in a rinse cleaning solvent comprising cyclic trihydrofluorocarbon as the principal component and being placed in rinse cleaning vessel 3. If necessary for improving the rinse cleaning power, therein, ultrasonic cleaning with ultrasonic oscillation apparatus 10 may be carried out concurrently with shower rinsing or shaking rinsing.

The cleaning agent deposited on the surface of the cleaning subject material is separated from the surface of the cleaning subject material. The separated cleaning agent is transferred, via rinse solution transfer pump 14 or overflowing or the flow of another additional rinse cleaning solvent, into separator 4 or distillation column 15.

In accordance with the invention, furthermore, the cyclic trihydrofluorocarbon as the principal component of the rinse cleaning solvent can exert high dissolution power of a cleaning agent in the high temperature zone, so heating with the heating apparatus 9 is preferable because the rinse cleaning effect is prominently improved then. Due to the supply of fresh cyclic trihydrofluorocarbon from circulation pump 11 or 12, the rinse cleaning solvent can be retained at a homogenous state in the rinse cleaning vessel 3, whereby no cleaning agent layer is formed on the upper layer; thus, the most serious conventional drawback of such type of apparatuses, namely re-deposition of the cleaning agent in the upper layer on the cleaning subject material when drawn out can be overcome. After use, the homogenous rinse cleaning solvent is transferred into the separator 4 or distillation column 15 in the same manner as described above.

In the separator 4, the upper layer of the cleaning agent layer 6 and the lower layer of the cyclic trihydrofluorocarbon layer 7 are separated from each other. By lowering the temperature of the separator 4, the purity of the recovered cyclic trihydrofluorocarbon can be elevated and the contamination of cyclic trihydrofluorocarbon into the hydrocarbon layer can be reduced, remarkably. Therefore, the two-layer separation procedure is generally carried out at a temperature lower by 10° C. or less, preferably 20° C. or less, more preferably 30° C. or less than the temperature of the rinse cleaning vessel 3.

The cyclic trihydrofluorocarbon layer 7 as the lower layer of the thus separated two layers is circulated via circulation pump 11 into rinse cleaning vessel 3 or via circulation pump 12 into vapor cleaning vessel 5.

Vapor cleaning is used when a high cleaning level is demanded or when the consumption of cyclic hydrofluorocarbon should be reduced. In this case, the cyclic hydrofluorocarbon recovered via the circulation pump 12 is transferred into vapor cleaning vessel 5 and heated with the heating apparatus 9, to form vapor zone 8. Alternatively, the cleaning subject material after drawn out from the rinse cleaning vessel 3 is vapor cleaned in the vapor zone 8 of the cyclic hydrofluorocarbon.

The cyclic hydrofluorocarbon used in vapor cleaning is transferred, through coagulation or overflowing, into rinse cleaning vessel 3, where the cyclic hydrocarbon is again used.

FIG. 1 schematically shows one example of the apparatus for use in carrying out the inventive cleaning method; and the details of the individual cleaning process, rinse cleaning process, two-layer separation process and vapor cleaning process are not limited to the embodiments described above. In accordance with the invention, other general methods can be used. If necessary, the numbers of cleaning and rinsing can be increased or decreased.

The action of the inventive fluorinated hydrocarbon or the cyclic trihydrofluorocarbon composing the same in cleaning for example is prominent from the respects of the cleaning potency and the stability. For example, the cleaning action of heptafluorocyclopentane (HFCPA) as cyclic trihydrofluorocarbon is at the same excellent level as that of octafluorocyclopentane (OFCPA) as dihydrofluorocarbon, while the stability thereof is far more greater than the stability of octafluorocyclopentane. Octafluorocyclopentane (OFCPA) is readily decomposable in the presence of basic compounds, water or heat.

Other than the application to cleaning as described above, the inventive fluorinated hydrocarbon and cyclic trihydrofluorocarbon composing the same, are as useful as liquid compositions for forming lubricating polymer film for electronic device, machine and apparatus. These hydrocarbons are used in liquid forms dispersing or dissolving polymers such as fluoropolymers, silicon containing resins, phenol resins, and polyolefin resins. In such manner, a polymer film capable of greatly reducing the frictional force against solid surface can be formed.

Polymers

In accordance with the invention, any polymer material with film forming potency is used with no specific limitation, as long as the material can form a film on solid surface. Herein the term film includes completely homgenous film in a continuous phase such as those formed from a polymer solution but also includes nearly homogenous film in an incompletely continuous phase of individual polymer particles, such as those formed from a dispersion of numerous polymer particles. It is not required that the polymer has specific properties. The polymer may satisfactorily have properties conventionally required for film formation, such as lubricating properties, non-coherent properties, or liquid repellency (water repellency or oil repellency).

The polymer with film forming property includes for example fluoropolymer, silicone resin, phenol resin, and polyolefin resin. Among them, preference is given to fluoropolymer.

Any fluoropolymer with a fluorine atom within the molecule is satisfactory, with no specific limitation, and includes for example fluoropolymers and chlorinated, fluorinated olefin polymers. Specific preferable examples of the fluorinated polymer include polytetrafluoroethylene (PTFE), tetrafluoroethylene-perfluoroalkyl vinyl ether copolymer (PFA), tetrafluoroethylene-hexafluoropropylene copolymer (FEP), tetrafluoroethylene-hexafluoropropylene-perfluoroalkyl vinyl ether copolymer (EPE), tetrafluoroethylene-ethylene copolymer (ETFE), polychlorotrifluoroethylene (PCTFE), chlorotrifluoroethylene-ethylene copolymer (ECTFE), polyvinyledene fluoride (PVDF) and polyvinyl fluoride (PVF). Among them, a homopolymer or copolymer or tetrafluoroethylene is preferable.

In accordance with the invention, fluoropolymers containing hetero atoms are preferably used. The hetero atoms mean atoms belonging to the Group 5B or 6B in the second to fourth periods in the periodic table, specifically including nitrogen atom, oxygen atom, sulfur atom and phosphorus atom. Oxygen atom is preferable. The fluorine-series polymers containing such hetero atoms include for example perfluoroalkylsulfonate polyesters, perfluoroalkyl polyethers, polyimides with perfluoroalkyl groups, and partially fluorinated modified silicon oils. Among them, perfluoroalkyl polyethers are particularly preferable.

Any of perfluoroalkyl polyethers for general use as materials for film formation is satisfactory, with no specific limitation; perfluoro-polyethers described in for example JP-A-61-126627, JP-A-63-97264, JP-A-4-211959, JP-A-5-342570 and JP-A-7-182652 can be used. Preferable perfluoro-polyethers include for example those represented by general formulas, such as $CH_2O-(CF_2CF_2O)n-CH_3$, $PhOCH_2OCH_2O-(CF_2CF_2O)n-CH_3$, $CF_3-[(OCF(CF_3)CF_2)n-(OCF_2)m]-OCF_3$, $CF_3-[(OCF_2CF_2)n-(OCF_2)m]-OCF_3$ wherein Ph represents phenyl group.

Additionally, fluoropolymers with cyclic structures in the principal chains thereof, including for example cyclic fluorochlorocarbon polymers prepared by substituting a part of the fluorine atoms in cyclic perfluorocarobn, cyclic perfluoroether or cyclic perfluorocarbon with chlorine atoms, can be used as well. Examples of the fluoropolymers with cyclic structures in the principal chains include polymers with various repeat units as represented by the following formulas.

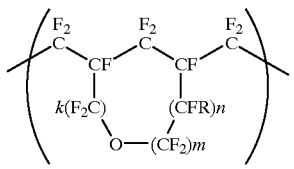

(wherein k=0 to 5; m=0 to 4; n=0 to 1; k+m+n=1 to 6; R represents F or $CF_3$.)

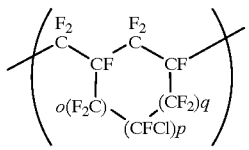

(wherein o, p, q=0 to 5; o+p+q=1 to 6.)

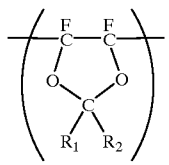

(wherein $R_1$ represents F or $CF_3$; $R_2$ represents F or $CF_3$.)

Specific examples of the repeat units as represented by the above mentioned individual general formulas include repeat units represented by the following formulas.

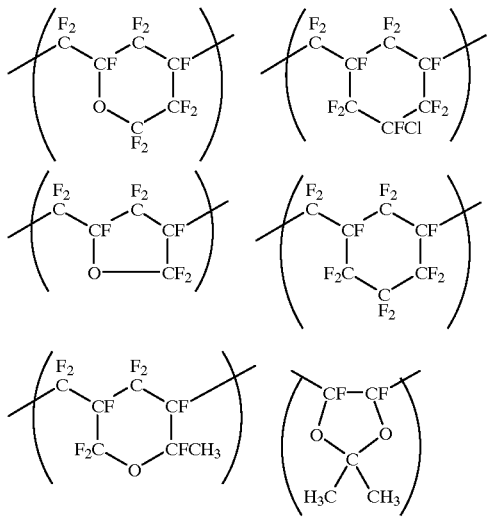

The cyclic perfluorocarbon and cyclic perfluoroether may satisfactorily be copolymerized with other monomers. Specific examples of the monomers to be copolymerized include.

| |
|---|
| $CF_2=CF\!-\!O\!-\!CF_2CF(CF_2)\!-\!O\!-\!CF_2CF_2SO_2F$, |
| $CF_2=CF\!-\!O\!-\!CF_2CF_2CF_2COOCH_3$, |
| $CF_2=CF\!-\!CF_3$, $CF(CF_3)_2\!-\!O\!-\!CF_2CF_2SO_2F$, |
| $NH_2CO(CH_2)_2Si(OC_2H_5)_3$ |

Additionally, the fluoropolymers include the polymers 1 to 9 described below, such as those described in JP-A-64-31642.

(1) Copolymer of $C_8F_{17}SO_2N$ $(C_3H_7)$ $CH_2CH_2OCOC(CH_3)=CH_2$ with fluorine-free alkyl methacrylate.
(2) Copolymer of $C_nF_{2n+1}CH_2CH_2OCOCH=CH_2$ (n=1 to 16) or $C_nF_{2n+1}CH_2OCOCH=CH_2$ (n=1 to 4) or $C_nF_{2n+1}OCOCH=CH_2$ (n=2 to 8) and methyl methacrylate at a molar ratio of 2:1 to 4:1.
(3) Polyurethane comprising $C_{10}F_{21}CH_2CH_2OH$, PPG-5000 and tolylene diisocyanate at a molar ratio of 2:1:2.
(4) Polyester comprising $C_8F_{17}SO_2N$ $(CH_2CH_2OH)_2$, polyethylene glycol and adipic acid at a molar ratio of 1:3:4.
(5) Copolymer of $CF_2=CFCl$, $CH_2=CH$ $(OC_2H_5)$ and $CH_2=CH$ $(O(CH_2)_2OH)$ at a molar ratio of 5:5:1.
(6) Copolymer of $CF_2=CFCl$ and $CH_2=CH_2$ at a molar ratio of 1:1.
(7) Copolymer of $CF_2=CFCF_3$ and $CH_2=CHOCH_3$ at a molar ratio of 1:1.
(8) Polyurethane comprising $HOCH_2CF_2O$ $(CF_2CF_2O)_{18}$ $(CF_2O)_{23}CF_2CF_2OH$, stearyl alcohol and tolylene diisocyanate at a molar ratio of 1:2:2.
(9) Unsaturated polyester comprising $(CF_3)_2C$ $(C_6H_4OH)_2$ or bisphenol A where at least one hydrogen atom in the phenol group is substituted with fluorine atom, adipic acid and fumaric acid at a molar ratio of 10:9:1.

The average molecular weight (number average molecular weight) of the fluorine-series polymer is with no specific limitation and is appropriately selected within a range of generally 1,000 to 5,000,000 preferably 1,000 to 1,000,000, more preferably 1,000 to 500,000. For example, the average molecular weight of the above mentioned perfluoroalkyl polyether is within a range of generally 1,000 to 100,000, preferably 1,000 to 50,000, more preferably 1,000 to 20,000. The molecular weights of the polymers 1 to 8 as described in JP-A-64-31642 are preferably 2,000 to 20,000 for polymer 1; 2,000 to 40,000 for polymer 2: about 5,900 for polymer 3; about 4,700 for polymer 4; about 3,000 for polymer 5;about 5,000 for polymer 6; about 8,000 for polymer 7; and about 15,000 for polymer 8. The liquid medium containing cyclic trihydrofluorocarbon for use in accordance with the invention so highly disperses polymer particles that these polymers may satisfactorily be dispersed in the form of particles. More specifically, by dispersing polymer particles in a liquid medium comprising a cyclic fluorinated hydrocarbon and coating the resulting dispersion on solid surface, thereby depositing the particles in dispersion in the form of film, a film of the polymer particles can be recovered, with great homogenous dispersibility of secondary particles, a small particle size distribution width of secondary particles, and a small frictional coefficient. The particle size of the polymer particles is appropriately selected, depending on the purpose of the use, but generally, the particle size is 0.1 to 50 μm; the particle size is within a range of preferably 0.01 to 10 μm, more preferably 0.01 to 5 μm.

A film can be formed by dissolving a polymer in a liquid medium containing cyclic trihydrofluorocarbon and coating the resulting solution on solid surface; in this case, however, the form of the polymer used is not specifically limited but includes a particle form, a grease form and a wax form.

The polymers with film formation potency can be used singly or in combination with two or more thereof.

Formulation ingredient

As disclosed in JP-A-7-182652 and JP-A-7-182653, formulation ingredients such as lubricating agents can be added to the polymers, if necessary, for the purpose of further reducing the frictional coefficients.

The lubricating agents include for example mineral oils such as paraffin oil, aroma oil, and naphthene oil; silicone oil; higher alcohols such as lauryl alcohol, tridecyl alcohol, cetyl alcohol, stearyl alcohol, oleyl alcohol, eicosyl alcohol and cetyl alcohol; higher fatty acids such as tridecanoic acid, myristic acid, pentadecanoic acid, palmitic acid, margaric acid, stearic acid, nonadecanoic acid, and arachic acid, and salts thereof with Li, Na, K, Mg, Ca and Ba; higher fatty acid esters such as methyl myristate, ethyl myristate, isopropyl pentadecanate, methyl palmitate, hexyl palmitate, butyl margarate, methyl stearate, ethyl stearate, propyl stearate, isopropyl stearate, butyl stearate, amyl stearate, isoamyl stearate, and hexyl stearate; and fluorine-containing silane compounds such as $CF_3(CH_2)_2Si(CH_3)Cl_2$, $CF_3(CH_2)_2Si(OCH_3)_3$, $CF_3(CF_{25}(CH_2)_2SiCl_3$, $CF_3(CF_{27}(CH_2)_2Si(CH_3)_2Cl$, $CF_3(CH_2)_7(CH_2)_2Si(OCH_2CH_3)_3$, $CF_3(CF_2)_5(CH_2)_2Si(NH_2)_3$. Among them, preference is given to mineral oil, silicon oil, higher alcohol, higher fatty acid, higher fatty acid salt and higher fatty acid ester.

The amount of the lubricating agent to be used is appropriately selected within a range with no deterioration of the characteristic properties of the resulting polymer film; the amount is generally 0.01 to 50 part(s) by weight, preferably 0.1 to 30 part(s) by weight, more preferably 1 to 15 part(s) by weight to 100 parts by weight of the polymer.

Coating subject solid

With no specific limitation, any solid can be used as a coating subject with a polymer-containing solution and is selected, depending on the purpose of the use. The materials of such coating subject solid include for example rubbers such as natural rubber, isoprene polymer, butadiene polymer rubber (BR), styrene-butadiene copolymer rubber (SBR), hydrogenated styrene-butadiene copolymer rubber (hydrogenated SBR), acrylonitrile-butadiene copolymer rubber (NBR), hydrogenated acrylochloroprene polymer rubber (CR), and silicon rubber; metals such as aluminum, iron stainless, titanium and copper; and inorganic materials such as SiO, SiC, carbon, glass, ceramics and silicon; and resins such as polycarbonate, polyimide, polysulfone, polyester, polyether sulfone polyester, polyphenylene sulfide, polyurethane, polyolefin, Bakelite, and polyacetal photosensitive resin.

The polymer-containing solution of the invention is useful in coating magnetic base materials.

As the magnetic base materials, use can be made of various non-magnetic base materials overlaid, directly or through an underlying layer such as nickel/phosphorus, titanium, silicon, and anodized aluminum, with a single ferromagnetic metal film or two or more such films.

As the ferromagnetic metal film, use can be made of Co, Co-Ni, Co-Cr, Co-Fe, Co-Ni-Cr, Co-Ni-Fe, Co-Ni-P and Co-Ni-Ta or partially oxidized forms thereof. These films can be formed by vacuum deposition, sputtering, ion plating and plating. If necessary, additionally, underlying layers of Cr or Ti may satisfactorily be arranged; and the thickness of the ferromagnetic metal film including the underlying layer is generally 0.005 $\mu$m to 100 $\mu$m, preferably 0.01 $\mu$m, to 50 $\mu$m.

If necessary, protective film layers generally used for general magnetic recording media can be formed on the surface of the ferromagnetic metal film, which is then put to use. As such protective layers, for example, the following layers can be formed; metal protective film layers of Cr, W, and Ni; inorganic protective film layers of SiO, SiC, carbon, graphite, and diamond-like carbon (JP-A-5-342570 and JP-A-61-126627); organic protective layers comprising linear saturated fatty acids with 8 to 28 carbon atoms, and salts thereof with alkali metals (Li, Na, K and the like) or alkali earth metals (Mg, Ca, Ba and the like) (JP-B-56-30609); silicone resin (JP-A-61-131231), epoxy resin, polyamide resin, plasma-induced polymerization product, and radiation-induced polymerization product; or complex protective layer. These protective films can be used singly or in combination with two or more layers overlaid together. The film thickness of the protective layer is appropriately selected, depending on the use, which is generally 0.01 to 0.1 $\mu$m, preferably 0.005 to 0.05 $\mu$m.

Specific examples of the coating subject solid comprising the materials described above, include inkjet record head, cleaning blade of office machines, for example rubber cleaning blade for removing residual toner on the photosensitive material of electrophotographic copy machine, the sliding parts of camera, office machines, medical apparatuses, precision machine, vacuum apparatuses such as vacuum pump, electronic parts, precision automobile parts, small motor, ultrasonic motor and micro-machine, magnetic record media of various magnetic disks such as hard disk and digital video tape, optical disk, and the space between film and rubber or resin sheet.

The form of the coating subject solid is not specifically limited, but specifically includes for example any of plate form, film form, particle form and fiber form.

Polymer-containing solution

So as to dissolve or disperse the polymer or the polymer together with a formulation ingredient in a solvent containing cyclic trihydrofluorocarbon, the polymer is placed in a liquid medium and agitated therein, satisfactorily. If necessary, means such as heating and ultrasonic irradiation can be used.

The content of the polymer in the inventive polymer-containing solution is appropriately selected, depending on the type of the polymer, the coating subject solid, the coating processability and the film thickness; the content is within a range of generally 0.0001 to 50% by weight, preferably 0.001 to 10% by weight, more preferably 0.005 to 5% by weight on the basis of the weight of solution (total weight of the liquid medium and the polymer). For coating on hard disk, for example, a solution at such a low concentration of 0.01 to 1% by weight is particularly preferable. Depending on whether or not the polymer is dissolved or dispersed in the liquid, the preferable concentration of the polymer varies. More specifically, when the polymer is dissolved in the liquid, the content is within a range of 0.0001 to 10% by weight, preferably 0.001 to 1% by weight, more preferably 0.005 to 0.5% by weight on the basis of the weight of solution (total weight of the liquid medium and the polymer). When the polymer is dispersed in the liquid, the content is within a range of generally 0.01 to 20% by weight, preferably 0.1 to 10% by weight, more preferably 0.5 to 5% by weight on the same basis.

Treatment of solid surface

A polymer film can be formed by coating the polymer-containing solution on solid surface and then removing the liquid medium.

The method for coating a dispersion or solution containing a polymer such as fluoropolymer is carried out in a conventional manner and includes for example, dipping, spin coating and spraying. The liquid medium contained in the coated film of the polymer-containing solution is generally removed by drying at ambient temperature or under heating in an inactive gas such as nitrogen gas or in atmosphere. Heating may be carried out in vacuum at a pressure of $10^{-1}$ Torr or less. Additionally, the removal of the liquid medium can be promoted by irradiation of light or electron beam for transferring the energy.

After drying the coated film, if desired, energy transfer from heat, light or electron beam can elevate the polymerization degree of film-composing polymers, such as fluoropolymers, or can induce cross linking therein.

The thickness of the polymer film is within a range of generally 0.0001 to 10 $\mu$m, preferably 0.0005 to 5 $\mu$m, more preferably 0.001 to 3 $\mu$m. Furthermore, the film thickness varies, depending on the use. The film thickness of the polymer film to be formed on inkjet record head is generally 0.001 to 10 $\mu$m, preferably 0.005 to 5 $\mu$m, and more preferably 0.01 to 2 $\mu$m; the film thickness of the polymer film to be formed on the cleaning blade of electrophotographic copy machine is generally 0.01 to 10 $\mu$m, preferably 0.01 to 5 $\mu$m, and more preferably 0.1 to 5 $\mu$m; and the film thickness of the polymer film to be formed on magnetic record hard disk is generally 0.0001 to 10 $\mu$m, preferably 0.0001 to 5 $\mu$m, and more preferably 0.0005 to 3 $\mu$m.

The invention is now more specifically described in the following examples. It is needless to say that the invention is not limited to these examples.

<SYNTHESIS>

EXAMPLE 1

(Synthesis of 1,1,2,2,3,3,4-heptafluorocyclopentane)

Octafluorocyclopentane (at a purity of 99.9%, 42.4 g, 200 mmol) and 5% palladium carbon (2.12 g) were charged in a 70 ml-autoclave fitted with an agitator, for hydrogenation a hydrogen pressure of 6 kg/cm$^2$ at 50° C. Fifteen hours later when hydrogen consumption was completely ceased, heating was terminated to stop the reaction. After sufficient neutralization with saturated sodium bicarbonate solution, the organic layer was separated, followed by addition of 200 ml of an aqueous sodium carbonate solution at a concentration of 1 mol. The resulting mixture was agitated at 30° C. for 10 hours. The reaction solution was separated into two layers; the resulting organic layer was again charged, together with 5% palladium carbon (1.78 g) and 1 g of tridecane, in a 70 ml-autoclave, for hydrogenation at 50° C. under a hydrogen pressure of 6 kg/cm$^2$. When hydrogen absorption was ceased 15 hours later, the reaction was terminated in the same manner as described above; then, the resulting solution was neutralized with saturated sodium bicarbonate solution, followed by distillation, to recover 1,1,2,2,3,3,4-heptafluorocyclopentane (at a purity of 99.0%; 34.0 g).

EXAMPLE 2

(Synthesis of 1,1,1,2,4,4,5,5,5-nonafluoropentane)

To 1,1,1,2,3,4,4,5,5,5-decafluoropentane (at a purity of 99.9%, 20 g, 79.4 mmol) was added 100 ml of an aqueous 4M potassium carbonate solution; and the resulting mixture was agitated at 30° C. for 10 hours. The reaction solution was separated into two layers; and the organic layer was again charged, together with 5% palladium carbon (0.55 g) and 0.33 g of tridecane, in a 70-ml autoclave, for hydrogenation at 50 ° C. under a hydrogen pressure of 6 kg/cm$^2$. When hydrogen absorption was ceased 15 hours later, the reaction was terminated; then, the resulting solution was neutralized with saturated sodium bicarbonate solution, followed by distillation, to recover nonafluoropentane (1,1,1,2,4,4,5,5,5- and 1,1,1,3,4,4,5,5,5-nonafluoropentane mixture)(at a total purity of 99.7%; 10.4 g).

<CLEANING>

EXAMPLE 3

Flux (PO-F-1010S; manufactured by Senju Kinzoku K.K.) was coated on the whole surface of a printed circuit board (30 mm ×30 mm×0.2 mm in thickness) made of a polyimide resin, which was then dried at ambient temperature. The resulting board was immersed in 1,1,2,2,3,3,4-heptafluorocyclopentane at a purity of 96% at 30° C. for 3 minutes. The extent of flux removal was visually observed. It was confirmed that the flux was completely removed.

EXAMPLE 4

Fifty sheets of a press-processed part (a 50-mm square made of stainless) were aligned together and bound with a wire; and the resulting stack was immersed in a beaker charged with a press oil (Daphne punch oil manufactured by Idemitsu Kosan, Co., Ltd.) at ambient temperature, followed by ultrasonic application for one minute so as to entirely immerse the stack in the press oil. After the stack was left to stand in the oil as it was for 30 minutes, the stack was drawn out of the press oil and left to stand for 5 minutes for oil draining. The sample was immersed in 1,1,2,2,3,3,4-heptafluorocyclopentane at a purity of 96% under ultrasonic application at 50° C. for 3 minutes and was further vapor cleaned in the vapor of 1,1,2,2,3,3,4-heptafluorocyclopentane at the same purity of 96%. After cooling, the extent of oil removal was visually observed, while the odor was checked. It was confirmed that the oil was completely removed.

EXAMPLES 5 to 8

COMPARATIVE EXAMPLES 1 to 8

Rosin-series fluxes (Table 2) were coated on printed circuit boards (1.6 mm×69 mm×95 mm) (Table 1), which were then dried preliminarily, followed by heating at 200° C. for 3 minutes. The resulting boards were used as test pieces.

These test pieces were immersed in 1,1,2,2,3,3,4-heptafluorocyclopentane (HFCPA) containing 10% ethanol at ambient temperature, for ultrasonic cleaning for one minute (at an output of 50%; 60 w and 35 kHz).

Alternatively, cleaning with CFC 113 and perfluorohexane was conducted in Comparative Examples.

The effect on the removal of the Rosin fluxes and the influence thereof on the print boards were visually observed; and the results are shown in Table 3.

Consequently, it is indicated that HFCPA containing 10% ethanol exerted the cleaning effect at the same level as or a higher level than the level of the cleaning performance of CFC 113 and PFC conventionally used.

TABLE 1

| Type name | Material |
| --- | --- |
| IC-301-62 | Phenol × PC |
| IC-701-62 | Glass epoxy | manufactured by Takasu Electronic Industries.

TABLE 2

| Name | Manufacturer |
| --- | --- |
| NS-829 | Nippon Superior Co., Ltd. |
| R5003 | Nippon Alpha-Metals, Co., Ltd. |

TABLE 3

| Test | Cleaning agent | Board material | Flux | Cleaning performance |
| --- | --- | --- | --- | --- |
| Example 5 | HPCPA | IC-301-62; phenol × PC | NS-829 | ◯ |
| Example 6 | HFCPA | IC-301-62; phenol × PC | R5003 | ◯ |
| Example 7 | HFCPA | IC-701-62; glass epoxy | NS-829 | ◯ |
| Example 8 | HFCPA | IC-701-62; glass epoxy | R5003 | ◯ |
| Comparative Example 1 | CFC 113 | IC-301-62; phenol × PC | NS-829 | ◯ |
| Comparative Example 2 | CFC 113 | 1C-301-62; phenol × PC | R5003 | ◯ |

TABLE 3-continued

| Test | Cleaning agent | Board material | Flux | Cleaning performance |
|---|---|---|---|---|
| Comparative Example 3 | CFC 113 | IC-701-62; glass epoxy | NS829 | ◯ |
| Comparative Example 4 | CFC 113 | IC-701-62; glass epoxy | R5003 | ◯ |
| Comparative Example 5 | perfluorohexane | 1C-301-62; phenol × PC | NS-829 | Δ - x |
| Comparative Example 6 | perfluorohexane | IC-301-62; phenol × PC | R5003 | Δ - x |
| Comparative Example 7 | Perfluorohexane | IC-701-62; glass epoxy | NS-829 | Δ - x |
| Comparative Example 8 | perfluorohexane | IC-701-62; glass epoxy | R5003 | Δ - x |

Cleaning performance: ◯; appropriate, Δ; poor, x; not good.

EXAMPLES 9 to 13

As shown in FIG. 1, a double-vessel cleaning machine (cleaning vessel 1 and cleaning vessel 2) equipped with heating apparatus 9 and ultrasonic oscillation apparatus 10 was charged with NS Clean 230 (a C13 hydrocarbon-series cleaning agent; manufactured by Nikko Petroleum Chemical Industries, Co.). The resulting vessel was designated as cleaning vessel; rinse cleaning machine (rinse cleaning vessel 3) equipped with heating apparatus 9 and ultrasonic oscillation apparatus 10 was charged with 1,1,2,2,3,3,4-heptafluorocyclopentane (HFCPA); furthermore, cyclic hydrofluorocarbon recovered in separator 4 was transferred into a vapor cleaning apparatus (vapor cleaning vessel 5) equipped with cooling tube 13 and was then heated with the heating apparatus 9, to generate vapor zone 8. Herein, the temperature of the separator 4 was controlled to 25° C.

Cleaning subject materials were prepared by dissolving staining substances in Table 4 at 25% in 1,1,1-trichloroethane, additionally adding a tracer sudan dye at 0.1% by weight to the resulting solution, and immersing materials shown in Table 4 in the resulting mixture to deposit the staining substances thereon. The amount of the staining substances deposited was determined, on the basis of the difference in weight between prior to and after immersion.

At subsequent cleaning tests of the cleaning subject materials, the materials were subjected to the following procedures sequentially in the cleaning vessel 1, cleaning vessel 2, rinse cleaning vessel 3 and vapor cleaning vessel 5.

1. Cleaning tank 1: cleaning subject materials were immersed in this vessel at 50° C., for 3-min ultrasonic application.
2. Cleaning vessel 2: cleaning subject materials were immersed in this vessel at 50° C. for 1-min ultrasonic application.
3. Rinse cleaning vessel 3: cleaning subject materials were immersed in this tank for 50° C., for 1-min ultrasonic application.
4. Vapor cleaning vessel 5: cleaning subject materials were placed in the vapor zone 8 of the vapor cleaning vessel 5 at 80° C. as the boiling point of the recovered 1,1,2,2,3,3,4-heptafluorocyclopentane (HFCPA) for 2 minutes.

After the cleaning tests, the cleaning subject materials were evaluated by the following methods. The results are also shown in Table 4.

<A>Amount of residual staining substances

After cleaning, the cleaning subject materials were treated with a given amount of purified 1,1,1-trichloroethane; extracting the residual staining substances and the dye and measuring the absorbance of sudan red, the residual amount thereof was determined on the basis of a standard curve. The residual amount divided by the amount of the measured deposited amount was shown as residual ratio (%).

<B>Visual evaluation

After cleaning, the cleaning subject materials were observed and assessed on the following standards.

O: no stain observed.

Δ: slight stain observed.

x: apparent stain observed.

<C>Evaluation of odor

After cleaning, the odor of the cleaning subject materials was checked and evaluated on the following standards.

O: no oil odor smelled.

Δ: slight oil odor smelled.

x: apparent oil odor smelled.

COMPARATIVE EXAMPLE 9

In the same manner as in Example 10 except that the rinse cleaning solvent was changed to vic-dihydrofluorocarbon, namely 1,1,1,2,2,3,4,5,5,5-decafluoropentane (DFPA; boiling point of 55° C.), a cleaning test was performed. The results are shown in Table 5.

COMPARATIVE EXAMPLE 10

In the same manner as in Example 10 except that the rinse cleaning solvent was changed to a perfluorocarbon, namely perflurohexane (PFHX; boiling point of 56° C.), a cleaning test was performed. The results are shown in Table 5.

TABLE 4

| Example | Materials | Stain | Residual amount | Visual observation | Odor |
|---|---|---|---|---|---|
| 9 | volt nut | cutting oil | 0.0% | ◯ | ◯ |
| 10 | glass epoxy resin | flux | 0.03% | ◯ | ◯ |
| 11 | glass bottle | silicone oil | 0.0% | ◯ | ◯ |
| 12 | printer blade | oily ink | 0.04% | ◯ | ◯ |
| 13 | optical glass lens | oil and fat | 0.0% | ◯ | ◯ |

TABLE 5

| Comparative Example | Fluorine-series solvent | Residual amount | Visual observation | Odor |
|---|---|---|---|---|
| 9 | 1,1,1,2,2,3,4,5,5,5-decafluoropentane | 0.25% | Δ | x |
| 10 | perfluorohexane | 0.5% | Δ | x |

Tables 4 and 5 indicate that the inventive examples (Examples 9 to 13) exerted great results at the assessment of residual amount of staining substances, visual assessment and odor assessment. On contrast, poor assessment results of residual amount of staining substances and odor are brought about when the linear hydrofluorocarbon was used as a rinse cleaning solvent (Comparative Example 9), indicating that the cleaning effect of the hydrofluorocarbon was not sufficient. Poor assessment results of residual amount of staining substances and odor are brought about when the perfluorocarbon was used as a rinse cleaning solvent (Comparative Example 10), indicating that the cleaning effect of the hydrofluorocarbon was not sufficient.

EXAMPLE 14

COMPARATIVE EXAMPLE 11

The cleaning methods in Example 9 and Comparative Example 10 were repeated 20 times; the cleaning power was then assessed; and the results are shown in Table 6.

TABLE 6

| Test | Fluorine-series solvent | Residual amount | Visual observation | Odor | Solution state *1 |
|---|---|---|---|---|---|
| Example 14 | 1,1,2,2,3,3,4-heptafluorocyclopentane | 0.01% | ○ | ○ | homogenous |
| Comparative Example 11 | 1,1,1,2,2,3,4,5,5,5-decafluoropentane | 0.5% | x | x | separation into two layers |

(*1: Visually observed whether or not the rinse cleaning solvent was homogeneously dissolved or was separated into two layers with a hydrocarbon layer as the upper layer.)

The results of Table 6 indicate that the inventive example (Example 14) can retain sufficiently great rinse cleaning effect even after use in repetition. On contrast, the rinse cleaning power was extremely deteriorated when the linear hydrofluorocarbon was used as a rinse cleaning solvent. This may be due to the fact that the rinse cleaning solvent was homogenous in Example 14, while in Comparative Example 11, the emerging hydrocarbon upper layer was possibly deposited again on the cleaning subject materials when they were drawn up.

<Polymers>

In the following examples and comparative examples, the polymer-containing solution and the method for forming a polymer film in accordance with the invention are now more specifically described. In the examples and comparative examples, the part and % are based on weight, unless otherwise stated.

Forming a polymer film on hard disk surface by using a polymer-containing solution with a polymer dissolved therein On an aluminium hard disk substrate of which the surface was plated with nickel in an electrolytic manner was arranged a cobalt alloy magnetic layer; 5 sheets of the hard disk, additionally arranged with a carbon layer of a thickness of about 200 angstroms, were vertically aligned at a given interval in an immersion tank; then, polymer-containing solutions described in Examples 15 and 18 and Comparative Examples 12 and 13 were heated at 35° C. and poured gradually in the tank. The polymer-containing solutions were poured at such a velocity that the entire surfaces of the hard disks might be immersed in the solutions over 2 minutes; after the hard disks were left to stand for 2 minutes, the hard disks were gradually drawn out of the immersion tank over 2 minutes. Subsequently, the hard disks were dried.

Evaluation of polymer film formed on hard disk surface by using polymer-containing solutions with polymers dissolved therein (1) Thickness of polymer film By using an inter-atomic force microscope, the thickness of polymer film was measured at 5 points along a line drawn from the disk center toward the circumference. For the measurement, etching a part of the polymer film formed on the hard disk surface with a solvent to remove the polymer, thereby exposing the underlining carbon layer to the hard disk surface, the resulting hard disk surface was defined as zero base for determining the thickness of polymer film. The results are shown in Table 7.

TABLE 7

| | Polymer thickness ($\times 10^{-4}$ $\mu$m) | | | |
|---|---|---|---|---|
| Test | maximum | minimum | mean of values at 5 points | Presence or absence of superficial wrinkle |
| Example 15 | 21 | 21 | 21 | no |
| Example 16 | 26 | 25 | 26 | no |
| Example 17 | 22 | 22 | 22 | no |
| Example 18 | 23 | 22 | 22 | no |
| Comparative Example 12 | 25 | 21 | 22 | many wrinkles along circumference direction |
| Comparative Example 13 | 55 | 22 | 28 | irregular, large recesses and protrusions with many wrinkles |

(2) Observation of Surface State of Polymer Film

By observing the hard disk surface with an inter-atomic force microscope, the presence or absence of wrinkles on the surface of a formed polymer film was observed. The results are shown in Table 7.

(3) CSS Test

After sufficiently drying the polymer film on the hard disk, the initial frictional coefficient was measured at a CSS number of 15,000, together with the CSS number when the initial frictional coefficient was increased, by using a CSS (contact start stop) tester. The results are shown in Table 8.

TABLE 8

| Test | Initial frictional coefficient | CSS number (recording CSS number when the initial frictional coefficient was increased) |
|---|---|---|
| Example 15 | 0.42 | The value of the initial frictional coefficient was maintained up to 15000. |
| Example 16 | 0.40 | The value of the initial frictional coefficient was maintained up to 15000. |
| Example 17 | 0.43 | The value of the initial frictional coefficient was maintained up to 15000. |
| Example 18 | 0.44 | The value of the initial frictional coefficient was maintained up to 15000. |
| Comparative Example 12 | 0.65 | about 12000. |
| Comparative Example 13 | large variation at about 1 to 3 | about 2500. |

Formation of Polymer Film on Rubber Sheet Surface by Using Polymer-Containing Solution With Polymer Dispersed Therein On a sheet of nitrile hydride rubber (acrylonitrile hydride-butadiene copolymer rubber, manufactured by Nippon Zeon) were coated dispersions described in Example 20 and Comparative example 14 by spraying; subsequently vaporizing and removing the solvents and further drying the sheet in hot air at 60° C. to disperse the polymer particles in a film form, a rubber sheet with a polymer film formed thereon was recovered.

Evaluation of Polymer Film on Rubber Sheet Surface, as Formed by Using Polymer-Containing Solution with Polymer Dispersed Therein (1) Average Film Thickness After sufficiently drying the polymer film on the rubber sheet, the film thickness of the polymer film was measured at arbitrary 5 points on the polymer film by means of eripsometer. The average film thickness is shown in Table 9.

TABLE 9

| | Example 19 | Comparative Example 14 |
|---|---|---|
| Mean film thickness ($\mu$m) | 1.9 | 8.7 |
| Dispersibility of polymer particles | | |
| dispersibility of secondary particle | homogenous | homogenous |
| particle size of secondary particle distribution width ($\mu$m) | about 1 to 3 | about 1 to 30 |
| Static frictional coefficient | | |
| 1 | 0.5 | 0.9 |
| 2 | 0.4 | 1.1 |
| 3 | 0.5 | 0.8 |
| 4 | 0.4 | 1.1 |
| 5 | 0.5 | 0.9 |
| Average | 0.46 | 0.96 |

(2) Dispersibility of Polymer Particles

After sufficiently drying the polymer film on the rubber sheet, the surface of the polymer film was observed by SEM; the dispersion state of secondary particles prepared by particle coherent as well as the particle size distribution of the secondary particles was evaluated. The results are shown in Table 9.

(3) Static Frictional Coefficient

After sufficiently drying the coated film of a fluorine-series polymer on the rubber sheet, 5 points were arbitrarily selected on the film surface; the static frictional coefficient at a sliding velocity of 1.5 mm/sec was measured at ambient temperature by using a friction tester of a pin-disk type. The results are shown in Table 9.

EXAMPLE 15

Demnum as a perfluoroether polymer (average molecular weight of 5600; manufactured by Daikin Industries, Co., Ltd.) was dissolved at a 0.2-% concentration in 1,1,2,2,3,3,4-heptafluorocyclopentane recovered in Example 1, which was defined as fluoropolymer-containing solution. By using the fluoropolymer-containing solution, a polymer film was formed on the hard disk, in the same manner as described above. The results shown in Table 7 indicate that the hard disk treated with the fluoropolymer-containing solution was at a small variation of the thickness of the fluoropolymer film, with no observed wrinkle on the surface. Additionally, even the results in Table 8 indicate that the hard disk treated with the fluoropolymer-containing solution had a small initial frictional coefficient, while the CCS number thereof indicates sufficient durability.

EXAMPLE 16

In the same manner as in Example 15 except for the use of Phonbrine (average molecular weight of 9500; manufactured by Audimont Co., Ltd.) as a perfluoroether polymer, experiments were carried out. The results in Table 7 indicate that the hard disk treated with the fluoropolymer-containing solution was at a small variation of the thickness of the fluorine-series polymer film, with no observed wrinkle on the surface. Additionally, the results in Table 8 indicates that the hard disk treated with the fluoropolymer-containing solution had a small initial frictional coefficient, while the CCS number thereof indicates sufficient durability.

EXAMPLE 17

In the same manner as in Example 15 except for the use of 1,1,2,2,3,3,4-heptafluorocyclopentane with addition of 10% by weight of nonafluorobutyl methyl ether (HFE-7100, manufactured by 3M) as the solvent for a polymer-containing solution, a polymer film was formed on the hard disk surface. The results in Table 7 show that that the hard disk treated with the fluorine-series polymer-containing solution was at a small variation of th thickness of the fluoropolymer film with no observed wrinkle on the surface. Additionally, the results in Table 8 indicate that the hard disk treated with the fluoropolymer-containing solution had a small initial frictional coefficient, while the CCS number thereof indicates sufficient durability.

EXAMPLE 18

In the same manner as in Example 15 except for the use of 1,1,2,2,3,3,4-heptafluorocyclopentane with addition of 10% by weight of 2,3,-dihydrodecafluoropentane (HFC-43-10 mee, manufactured by Dupont, Co.) as the liquid medium for a polymer-containing solution, a polymer film was formed on the hard disk surface. The results in Table 7 show that that the hard disk treated with the fluoropolymer-containing solution was at a small variation of the thickness of the fluoropolymer film, with no observed wrinkle on the surface. Additionally, the results in Table 8 indicate that the hard disk treated with the fluoropolymer-containing solution had a small initial frictional coefficient, while the CCS number thereof indicates sufficient durability.

COMPARATIVE EXAMPLE 12

In the same manner as in Example 15 except for the use of perfluoro-n-pentane instead of 1,1,2,2,3,3,4-heptafluorocyclopentane as the liquid medium for a polymer-containing solution, a fluoropolymer film was formed on the hard disk surface. The results in Table 7 indicate that wrinkles were observed on the surface of the hard disk treated with the fluoropolymer-containing solution along the circumference direction, with a variation of the thickness of the fluoropolymer film. Furthermore, the results of the CCS test (Table 8) show that the frictional coefficient of the hard disk treated with the fluorine-series polymer-containing solution was larger than that in Example 1. Still furthermore, the initial frictional coefficient was increased at a CSS number of about 12,000, with no sufficient durability as observed in Example 15.

COMPARATIVE EXAMPLE 13

In the same manner as in Example 16 except for the use of perfluoro-n-pentane instead of 1,1,2,2,3,3,4- heptafluorocyclopentane as the liquid medium for a polymer containing solution, a fluoropolymer film was formed on the hard disk surface. At the stage of polymer dissolution, however, the polymer-containing solution turned turbid, which indicates that the polymer was not homogeneously dissolved therein. The results in Table 7 indicate that the thickness of the fluoropolymer film was at a large variation and that wrinkles were significant together with the presence of large recesses and protrusions on the surface of the hard disk treated with the fluoropolymer-containing solution. Furthermore, the results of the CCS test (Table 8) show that the initial frictional coefficient of the hard disk treated with the fluoropolymer-containing solution was increased at a CSS number of about 2500, with no sufficient durability as observed in Example 15.

EXAMPLE 19 AND COMPARATIVE EXAMPLE 14

Polytetrafluoroethylene particle (mean particle size of 0.5 μm) was dispersed in a solvent composed of 95 parts by weight of 1,1,2,2,3,3,4-heptafluorocyclopentane recovered in Example 1 and 5 parts by weight of nonafluorobutyl methylether (HFE-7100 manufactured by 3M, Co.), to prepare a polymer-containing solution in dispersion at a solid concentration of 1.0%. The dispersion was dispersed and deposited in a film form on the rubber sheet, to prepare a polymer film. The characteristic properties of the polymer particle film were evaluated. The results are shown in Table 9.

In Comparative Example 14, a polymer film was formed on the rubber sheet in the same manner as in Example 19, except for the use of perfluoro-n-heptane instead of the mixture of 1,1,2,2,3,3,4-heptafluorocyclopentane and nonafluorobutyl methyl ether. The characteristic properties of the polymer particle film were evaluated. The results are shown in Table 9.

As shown in Table 9, in the case of coating dispersions prepared by dispersing polymer particles in the inventive liquid medium containing trihydrofluorocarbon on solid surface to disperse and deposit the particles in a film form (Example 19), compared with the case of the linear fluorine-series hydrocarbon used as the liquid medium (Comparative Example 14), a polymer film with a smaller average film thickness, more homogenous dispersibility of secondary particles, a smaller particle size distribution width and a smaller static frictional coefficient can be recovered.

<Stability Test of Trihydrofluorocarbon>
Stability Test in Alkali

REFERENCE EXAMPLE 1

In a Pyrex glass tube (15 ml) were placed 1,1,2,2,3,3,4-heptafluorocyclopentane (at a purity of 98.3%, 1.0 g), an aqueous potassium carbonate solution (at a concentration of 4 mol/l, 1.5 ml) and tetrabutylammonium bromide (50 mg), and the resulting mixture was agitated at 30° C. in a water bath. Two hours later, agitation was ceased; and the lower layer was analyzed by gas chromatography (263–70 manufactured by Hitachi, Co., Ltd.). The results indicate that the decomposition ratio of 1,1,2,2,3,3,4-heptafluorocyclopentane was 19.5%.

REFERENCE EXAMPLE 2

In a Pyrex glass tube (15 ml) were placed 1,1,1,2,3,4,4,5,5,5-decafluoropentane (1.0 g), an aqueous potassium carbonate solution (at a concentration of 4 mol/l, 1.5 ml) and tetrabutylammonium bromide (50 mg), and the resulting mixture was agitated at the same velocity as in Reference Example 1 at 30° C. in a water bath. Two hours later, agitation was ceased; and the lower layer was analyzed by gas chromatography (263–70, manufactured by Hitachi, Co., Ltd.). The results indicate that the decomposition ratio of 1,1,1,2,3,4,4,5,5,5-decafluoropentane was 40%.

REFERENCE EXAMPLE 3

In the same manner as in Reference Example 2 except for the use of nonafluoropentane synthetically produced in Example 2, instead of 1,1,1,2,3,4,4,5,5,5-decafluoropentane, experiments were carried out. Then, the decomposition ratio of nonafluoropentane was 18%.

REFERENCE EXAMPLE 4

In the same manner as in Reference Example 1 except for the use of 1,1,2,2,3,3,4,5-octafluorocyclopentane instead of 1,1,2,2,3,3,4-heptafluorocyclopentane, experiments were carried out. Then, the decomposition ratio of octafluorocyclopentane was 56.9%.

REFERENCE EXAMPLE 5

A mixture (10 g) of 65 parts by weight of 1,1,2,2,3,3,4,5-octafluorocyclopentane instead of 1,1,2,2,3,3,4-heptafluorocyclopentane and 35 parts by weight of 1,1,2,2,3,3,4-heptafluorocyclopentane, an aqueous potassium carbonate solution (at a concentration of 2.5 mol/l, 1.2 equivalents to 1,1,2,2,3,3,4,5-octafluorocyclopentane), and tetrabutylammonium bromide (at 5% by weight of OFCPA) were placed, and the resulting mixture was agitated at the same velocity as in Reference Example 1 at 30° C. in a water bath. Two hours later, agitation as ceased; and the lower layer was analyzed by gas chromatography (263–70, manufactured by Hitachi, Co., Ltd.). The results indicate that the decomposition ratio of 1,1,2,2,3,3,4,5-octafluorocyclopentane was 100%, while the decomposition ratio of 1,1,2,2,3,3,4-heptafluorocyclopentane was 1.8%.

REFERENCE EXAMPLE 6

In a glass evaporation dish was placed 2 g of 1,1,2,2,3,3,4-heptafluorocyclopentane (at a purity of 98.3%), to which the flame of a hand-type gas burner was brought close. The fluid was only evaporated by never burned.

REFERENCE EXAMPLE 7

In a glass evaporation dish was placed 2 g of 1,1,2,2,3,3-hexafluorocyclopentane (at a purity of 99.9%), to which the flame of a hand-type gas burner was brought close. The fluid burned with red flame, and thereafter, the flame disappeared. Soot was deposited on the wall surface of the evaporation dish.

REFERENCE EXAMPLE 8

In a glass evaporation dish was placed 2 g of 1,1,2,2,3,3,4-heptafluorocyclopentane (at a purity of 98.3%) and 10 mg of Demnum as the perfluoroether-series polymer used in Example 16, to which the flame of a hand-type gas burner was brought close. The fluid was only evaporated by never burned.

By the same method as described above, 1,1,2,2,3,3-hexafluorocyclopentane (at a purity of 99.9%) was tested. The fluid burned with red flame, and thereafter, the flame disappeared. Soot was deposited on the wall surface of the evaporation dish.

The results indicate that the incombustibility of the polymer-containing solution in the liquid medium 1,1,2,2,3,3,4-heptafluorocyclopentane was elevated, compared with the incombustibility of a polymer-containing solution in a liquid medium of tetrahydrofluorocarbon with a structure —$CH_2$—$CH_2$—, such as 1,1,2,2,3,3-hexafluorocyclopentane.

Purification and Recovery in Separator 4

REFERENCE EXAMPLE 9

In a 200-ml flask with a magnetic agitator was placed a mixture of 10 g of n-tridecane and 100 ml of 1,1,2,2,3,3,4-heptafluorocyclopentane, and the temperature of the mixture was gradually elevated under agitation to heat the mixture to 75° C. and prepare a homogenous solution. Subsequently, the homogenous solution was transferred in the separator 4 in FIG. 1 (at 20° C.). The solution turned opaque and was later separated completely into two layers. The lower layer was analyzed by gas chromatography. The purity of 1,1,2,2,3,3,4-heptafluorocyclopentane was 98%, which indicates that the solvent was almost entirely purified and recovered.

Industrial Applicability

As has been described above in detail, the invention of the application can provide a fluorinated hydrocarbon comprising a highly pure cyclic trihydrofluorocarbon, characterized in that the fluorinated hydrocarbon with excellent cleaning action, incombustibility and high stability in the presence of basic compounds and water, can be produced readily, a composition thereof, and a cleaning agent and a cleaning method.

The fluorinated hydrocarbon in accordance with the invention of the application can absolutely be used as a cleaning agent, a rinse cleaning agent, a vapor cleaning agent, a gap cleaning agent, and an agent for water draining and cleaning.

Additionally, specific utilities thereof include for example various test solvents such as solvent for switch withstand voltage, solvent for ceramic depolarization test, solvent for Braun tube socket withstand voltage, and solvent for film condenser withstand voltage; liquid medium for rectifier; liquid medium for transformer; liquid medium for condenser; cooling and heating liquid medium for cooling semiconductor production apparatuses and dry etching apparatuses, ozone apparatus, liquid crystal projector, and power source heat exchanger; solvent for producing fluorine polymers; solvent for forming film from fluorinated silicon polymer; cleaning agent of hollow fiber; dry cleaning solvent; solvent for fluorine-containing electrolytes; optical disk, magnetic disk; solvent for forming surface lubricating layer on magnetic disk and magnetic tape; solvent for checking crack or leakage in castings and ceramic products; solvent for chemical reactions including reaction with Lewis acid catalysts and the like; hollow cleaning solvent; disk polishing solvent for silicon wafer substrate, metal substrate and glass substrate; cleaning agent for the production of semiconductor IC chip; surface treating solvent of printed circuit board; solvent for chemical mechanical polishing; solvent for photoresist; solvent for developing solution; and rinse solution composition. The inventive fluorinated hydrocarbon can be used as a medical medium, such as aerosol medium for humans, including dosage forms such as external dosage forms of anti-inflammatory agents, therapeutic agents of muscle fatigue, topical heating agents, analgesic agents, blood circulation promoting agents, coating and spreading dosage forms on human skin, inhalation agents, intra-nasal droplets, anti-odor agents, sterilizers, and cleaning and wiping agents; sterilization and cleaning agents of hollow fiber for dialysis; cooling medium for medical cooling apparatuses for cryoperation and medical treatment of head, by means of catheters; polymer-containing solution for forming polymer film on the surface of disposable products such as catheter, implants, guide wire, circuit and sensor and of implants such as artificial blood tube, stent, and artificial bone; cleaning agent for disposable products such as catheter, insertion device, guide wire, injection needle, circuit, bag and sensor, implants such as artificial blood tube, stent, artificial bone and dental materials, and rigid devices such as tongs, scissors, tweezers, and thoracotomy device; pressurized medium for administering a trace amount of drug in a sustained manner to a lesion; solvent for producing gelatin capsule carrying drug; solvent for lubricant application during medical catheter production and solvent for lubricant removal; and solvent for lubricant application on artificial organs and artificial blood tube and solvent for lubricant removal from these organs.

By dissolving or dispersing a polymer with film forming potency in a liquid medium principally containing trihydrofluorocarbon, and coating the resulting polymer-containing solution of the invention of the application on solid surface thereby forming a polymer film, the resulting polymer film is of a film thickness at a very high uniformity.

In accordance with the invention of the application, the essential characteristic properties of the polymer, such as lubrication properties, non-coherent properties and liquid repellency, can be improved more.

Thus, the polymer-containing solution of the invention of the application is useful for the formation of a water repellent film on inkjet record head and is also useful for the formation of a polymer film with lubrication properties and non-coherent properties on cleaning blade of inkjet record head and office machines, for example rubber cleaning blade for removing residual toner on the photosensitive material of an electrophotographic copy machine, and the sliding parts of camera, office machine, medical apparatuses, precision machines, vacuum apparatuses such as vacuum pump, electronic parts, precision automobile parts, small motor, ultrasonic motor, and micro-machine and on magnetic record media such as hard disk and optical disk.

What is claimed is:

1. A product containing 95 wt % of more of cyclic trihydrofluorocarbon with 5 carbon atoms as represented by the following formula I:

$$Rf_1—R_1—Rf_2 \qquad (I)$$

wherein $R_1$ represents a carbon chain of CHF and $CH_2$, bound to each other, and $Rf_1$ and $Rf_2$ bind to each other to form a perfluoroalkylene ring.

2. A product according to claim 1, containing 99% or more of the trihydrofluorocarbon represented by the formula I.

3. A cleaning agent containing a product as the effective ingredient according to any one of claims 1 or 2.

4. A method for cleaning an article with staining substances deposited thereon, comprising removing the staining substances from the article by putting the article in contact with an organic solvent comprising at least one selected from hydrocarbons, alcohols, esters, chlorinated hydrocarbons, other fluorinated hydrocarbons, ethers, ketones, and volatile organic silicons, and rinse cleaning such article comprising putting the organic solvent deposited on the article after the removal of the staining substances in contact with a cleaning agent according to claim 3, thereby rinse cleaning the article, or comprising vapor rinsing the article in the vapor of the cleaning agent.

5. A polymer-containing solution prepared by dissolving or dispersing a polymer with film-forming potency in a product according to any one of claims 1 or 2.

6. A polymer-containing solution according to claim 5, wherein the polymer with film-forming potency is at least one selected from fluoropolymers, silicon resin, phenol resin, and polyolefin resin.

7. A method for forming a polymer film on the surface of a solid, comprising coating a polymer-containing solution according to claim 6, on the surface of the solid and removing the liquid medium.

8. A method for forming a polymer film on the surface of a solid, according to claim 7, wherein the solid is magnetic record medium, optical disk, cleaning blade, or inkjet record head.

9. A polymer-containing solution according to claim 5, wherein the polymer with film-forming potency has at least one property selected from lubrication properties, non-coherent properties and liquid repellency.

10. A method for forming a polymer film on the surface of a solid, comprising coating a polymer-containing solution according to claim 9, on the surface of the solid and removing the liquid medium.

11. A method for forming a polymer film on the surface of a solid, according to claim 10, wherein the solid is magnetic record medium, optical disk, cleaning blade, or inkjet record head.

12. A polymer-containing solution according to claim 5, wherein the polymer-containing solution contains a lubricant comprising at least one selected from mineral oil, silicone oil, higher alcohol, higher fatty acid and salts thereof, higher fatty acid ester and fluorine-containing silicon compound.

13. A polymer-containing solution according to claim 12, wherein the lubricant is used at an amount of 0.01 to 50 parts by weight to 100 parts by weight of the polymer.

14. A method for forming a polymer film on the surface of a solid, comprising coating a polymer-containing solution according to claim 13, on the surface of the solid and removing the liquid medium.

15. A method for forming a polymer film on the surface of a solid, according to claim 14, wherein the solid is magnetic record medium, optical disk, cleaning blade, or inkjet record head.

16. A method for forming a polymer film on the surface of a solid, comprising coating a polymer-containing solution according to claim 12, on the surface of the solid and removing the liquid medium.

17. A method for forming a polymer film on the surface of a solid, according to claim 16, wherein the solid is magnetic record medium, optical disk, cleaning blade, or inkjet record head.

18. A method for forming a polymer film on the surface of a solid, comprising coating a polymer-containing solution according to claim 5, on the surface of the solid and removing the liquid medium.

19. A method for forming a polymer film on the surface of a solid, according to claim 12, wherein the solid is magnetic record medium, optical disk, cleaning blade, or inkjet record head.

20. A method for producing a fluorinated hydrocarbon, comprising subjecting a dihydrofluorocarbon represented by the following formula II to an alkali treatment and subsequently hydrogenating the resulting product:

$$Rf_1\text{—}CHF\text{—}CHF\text{—}Rf_2 \qquad (II)$$

wherein $Rf_1$ and $Rf_2$ independently represent a perfluoroalkyl group and $Rf_1$ and $Rf_2$ may be bound to each other, to form a ring.

21. A method for producing a fluorinated hydrocarbon according to claim 20, wherein the dihydrofluorocarbon represented by the formula II is an alicyclic compound.

22. A method for producing a fluorinated hydrocarbon according to claim 20, wherein the alkali for the alkali treatment of the dihydrofluorocarbon represented by the formula II is at least one selected from metal hydrogen carbonate salts, metal carbonate salts, hydroxides and anion exchange resins and the amount thereof to be used is an equivalent or more to 1 mole of the dihydrofluorocarbon.

23. A method for producing a fluorinated hydrocarbon according to claim 20, wherein the pressure for the hydrogenation reaction subsequent to the alkali treatment is atmospheric pressure to 10 kgf/cm$^2$ and the reaction temperature is ambient temperature to about 350° C.

24. A fluorinated hydrocarbon composition containing a product according to any one of claims 1 or 2 and at least one organic solvent at a boiling point of 25° C. or more to 250° C. or less.

25. A fluorinated hydrocarbon composition according to claim 24, wherein the organic solvent is added at an amount of 50% by weight or less to the total weight.

26. A fluorinated hydrocarbon composition according to claim 25, wherein the organic solvent is added at an amount of 2 to 30% by weight to the total weight.

27. A cleaning agent containing a fluorinated hydrocarbon composition as the effective ingredient according to claim 26.

28. A polymer-containing solution prepared by dissolving or dispersing a polymer with film-forming potency in a fluorinated hydrocarbon composition according to claim 26.

29. A cleaning agent containing a fluorinated hydrocarbon composition as the effective ingredient according to claim 25.

30. A polymer-containing solution prepared by dissolving or dispersing a polymer with film-forming potency in a fluorinated hydrocarbon composition according to claim 25.

31. A fluorinated hydrocarbon composition according to claim 24, wherein the organic solvent is at least one selected from hydrocarbons, alcohols, esters, chlorinated hydrocarbons, other fluorinated hydrocarbons, ethers, ketones, and volatile organic silicons.

32. A cleaning agent containing a fluorinated hydrocarbon composition as the effective ingredient according to claim 31.

33. A polymer-containing solution prepared by dissolving or dispersing a polymer with film-forming potency in a fluorinated hydrocarbon composition according to claim 31.

34. A fluorinated hydrocarbon composition according to claim 24, wherein the composition is an azeotropic composition.

35. A fluorinated hydrocarbon composition according to claim 34, wherein organic solvents forming the azeotropic composition are lower alcohols, hydrocarbons, chlorinated hydrocarbon, and other fluorinated hydrocarbons.

36. A cleaning agent containing a fluorinated hydrocarbon composition as the effective ingredient according to claim 35.

37. A polymer-containing solution prepared by dissolving or dispersing a polymer with film-forming potency in a fluorinated hydrocarbon composition according to claim 35.

38. A cleaning agent containing a fluorinated hydrocarbon composition as the effective ingredient according to claim 34.

39. A polymer-containing solution prepared by dissolving or dispersing a polymer with film-forming potency in a fluorinated hydrocarbon composition according to claim 34.

40. A cleaning agent containing a fluorinated hydrocarbon composition as the effective ingredient according to claim 24.

41. A method for cleaning an article with staining substances deposited thereon, comprising removing the staining substances from the article by putting the article in contact with an organic solvent comprising at least one selected from hydrocarbons, alcohols, esters, chlorinated hydrocarbons, other fluorinated hydrocarbons, ethers, ketones, and volatile organic silicons, and rinse cleaning such article comprising putting the organic solvent deposited on the article after the removal of the staining substances in contact with a cleaning agent according to claim 40, thereby rinse cleaning the article, or comprising vapor rinsing the article in the vapor of the cleaning agent.

42. A polymer-containing solution prepared by dissolving or dispersing a polymer with film-forming potency in a fluorinated hydrocarbon composition according to claim 24.

43. A polymer-containing solution according to claim 42, wherein the polymer with film-forming potency is at least one selected from fluoropolymers, silicon resin, phenol resin, and polyolefin resin.

44. A polymer-containing solution according to claim 42, wherein the polymer with film-forming potency has at least one property selected from lubrication properties, non-coherent properties and liquid repellency.

45. A polymer-containing solution according to claim 42, wherein the polymer-containing solution contains a lubricant comprising at least one selected from mineral oil, silicone oil, higher alcohol, higher fatty acid and salts thereof, higher fatty acid ester and fluorine-containing silicon compound.

46. A polymer-containing solution according to claim 45, wherein the lubricant is used at an amount of 0.01 to 50 parts by weight to 100 parts by weight of the polymer.

47. A method for forming a polymer film on the surface of a solid, comprising coating a polymer-containing solution according to claim 43, on the surface of the solid and removing the liquid medium.

48. A method for forming a polymer film on the surface of a solid, according to claim 47, wherein the solid is magnetic record medium, optical disk, cleaning blade, or inkjet record head.

* * * * *